US012779181B2

(12) United States Patent
Rattner

(10) Patent No.: US 12,779,181 B2
(45) Date of Patent: Nov. 3, 2026

(54) DEVICE AND METHOD TO EXTEND THE LIFETIME OF A VENOUS PATHWAY FOR CATHETER ACCESS

(71) Applicant: Zachary Rattner, Rancho Santa Fe, CA (US)

(72) Inventor: Zachary Rattner, Rancho Santa Fe, CA (US)

( * ) Notice: Subject to any disclaimer, the term of this patent is extended or adjusted under 35 U.S.C. 154(b) by 177 days.

(21) Appl. No.: 18/439,985

(22) Filed: Feb. 13, 2024

(65) Prior Publication Data

US 2024/0350776 A1 Oct. 24, 2024

Related U.S. Application Data

(60) Provisional application No. 63/461,044, filed on Apr. 21, 2023.

(51) Int. Cl.

| | |
|---|---|
| ***A61M 25/09*** | (2006.01) |
| ***A61B 17/34*** | (2006.01) |
| ***A61M 25/00*** | (2006.01) |
| ***A61M 39/06*** | (2006.01) |

(52) U.S. Cl.

CPC ... *A61M 25/09041* (2013.01); *A61B 17/3415* (2013.01); *A61M 25/0097* (2013.01); *A61M 39/0613* (2013.01)

(58) Field of Classification Search

CPC ........... A61B 17/3415; A61B 17/3462; A61M 2025/0293; A61M 25/0097; A61M 25/09041; A61M 39/0613; A61M 39/0208; A61M 39/022; A61M 39/0223; A61M 39/0235

See application file for complete search history.

(56) References Cited

U.S. PATENT DOCUMENTS

| | | | | |
|---|---|---|---|---|
| 5,498,240 A * | 3/1996 | Bagaoisan .......... | A61M 25/104 604/523 |
| 7,578,803 B2 * | 8/2009 | Rome ............... | A61M 39/0606 604/167.03 |
| 2007/0149949 A1 * | 6/2007 | Porter ............... | A61M 39/0247 604/523 |
| 2009/0149838 A1 * | 6/2009 | Cassada ............ | A61M 25/0021 604/890.1 |
| 2016/0015570 A1 * | 1/2016 | Heinecke ............ | A61F 13/0236 602/58 |
| 2017/0182304 A1 * | 6/2017 | Bagwell ............ | A61M 39/0247 |

FOREIGN PATENT DOCUMENTS

WO WO-2007112520 A2 * 10/2007 ............ A61M 39/04

OTHER PUBLICATIONS

WO-2007112520 English machine translation (Year: 2007).*

* cited by examiner

*Primary Examiner* — Nathan R Price
*Assistant Examiner* — Katerina A. Wittliff
(74) *Attorney, Agent, or Firm* — Robert E. Colletti; Haug Partners LLP

(57) ABSTRACT

The invention provides a method and device to maintain catheter access durably and safely in a patient who may need intermittent percutaneous catheter placements, such as a patient undergoing hemodialysis (HD). The system includes an easily and quickly implantable fully internal catheter device that acts as a place keeper for a venous access pathway that otherwise may be lost over time. In embodiments, the device functions as a portacath, which can be accessed percutaneously to be used for blood draws and intravenous drug administrations.

30 Claims, 13 Drawing Sheets

FIG. 7a
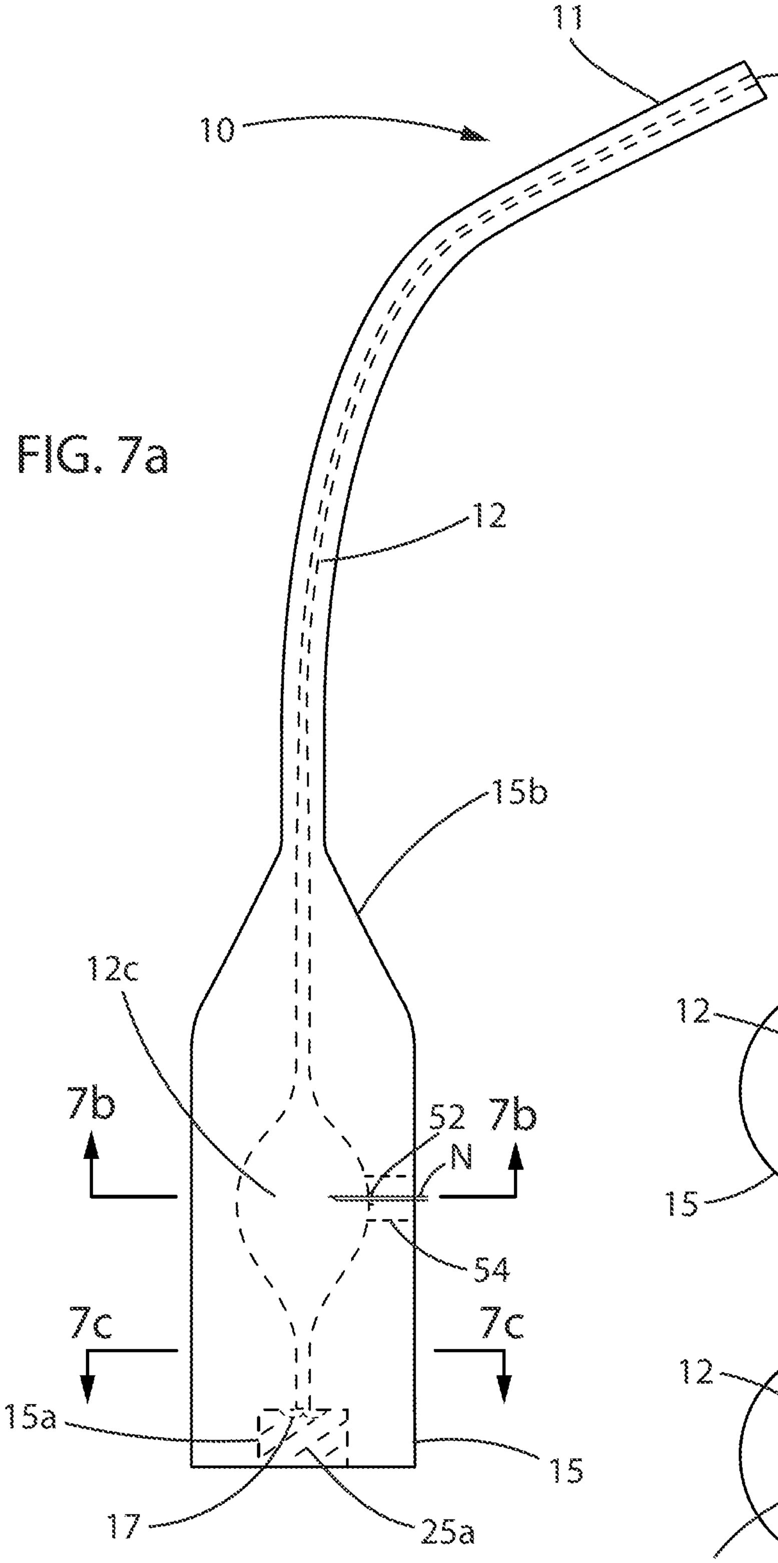
FIG. 7b
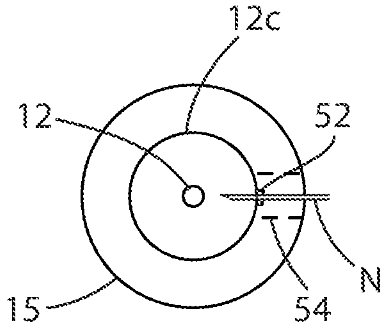
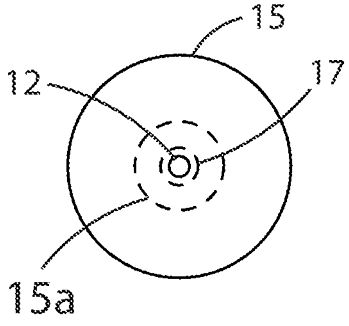
FIG. 7c

DEVICE AND METHOD TO EXTEND THE LIFETIME OF A VENOUS PATHWAY FOR CATHETER ACCESS

CROSS-REFERENCE TO RELATED APPLICATION(S)

This application claims benefit to U.S. Provisional Application Ser. No. 63/461,044, filed Apr. 21, 2023, which is hereby incorporated by reference herein in its entirety.

FIELD OF THE INVENTION

The present invention relates to maintaining intravenous access for catheter placements. It has particular value for patients undergoing hemodialysis, who may need catheter placements periodically over a period of years.

BACKGROUND

Hemodialysis patients require a mechanism to permit rapid exchange of circulating blood with a hemodialysis machine. This can be accomplished via establishment of a fistula or a graft, usually placed in an upper extremity, or a catheter designed for this purpose, usually placed in the chest.

Many patients receive a catheter at the time of a diagnosis of kidney failure to initiate hemodialysis. An advantage of a catheter in this setting is that it can be implanted quickly, and dialysis can be performed immediately after implantation.

Catheters can be tunneled or non-tunneled. While a non-tunneled catheter may be used briefly, it has a significant risk of infection if used longer than several days, so patients entering chronic end-stage renal disease most commonly receive a tunneled hemodialysis catheter.

Tunneled catheters generally have an external back end (proximal) with split arterial and venous hubs that join to form a single common catheter (distal) with arterial and venous lumens. When implanted in patients P (see FIG. 4A), these catheters most commonly enter the skin through a small chest wound incision Ia under the clavicle, then course under the skin to a large vein to enter the venous system, usually a jugular vein. The distal portion of the catheter passes from the jugular vein to a more central vein, usually the superior vena cava or right atrium. The subcutaneous and intravenous portions of the catheter may be termed internal, and the catheter used for HD may be referred to as an internal/external catheter C.

Generally, tunneled HD catheters are only used for weeks to months. As soon as possible, dialysis patients receive access systems that are safer in the longer-term, such as fistulas and grafts, and the catheter is removed. Fistulas and grafts, which have no external component, are preferred to catheter access due to lower rates of infection and mortality. Further, patients generally prefer not to have the restrictions associated with an internal/external catheter C, which extends through the skin and has a bulky external hub.

Over the course of a HD lifetime, most patients periodically need additional catheter placements. For various reasons, fistulas and grafts fail and need revision or replacement, a process that can take weeks or months. When this occurs, the patient requires placement of a new HD catheter, which is maintained until there is again a functioning graft or fistula. Therefore, over the course of HD treatment, most patients require multiple catheter placements.

Each time a catheter is placed, there can be injury to the veins it enters and crosses. This occurs when there is peri-catheter thrombosis and, with time, a scarring down of the vein, or intimal hyperplasia. For example, the most common venous entry point for a hemodialysis catheter is generally the right internal jugular vein (IJV). After a relatively short period, thrombus often forms in a right IJV and more centrally in the right brachiocephalic vein. With time, thrombosis and intimal hyperplasia of the vein lining can narrow the vein lumen substantially, sometimes to the point that the HD catheter is occlusive.

When the HD catheter is removed from a vein pathway that has experienced thrombosis and intimal hyperplasia, the pathway may occlude completely. As a result, the next time a patient needs a new catheter placed, even a skilled practitioner may not be able to place it through the same vein pathway. If the practitioner is fortunate and can cross the occlusion with a small-diameter interventional catheter and guidewire 22, it is generally straightforward to dilate the pathway and eventually deliver a hemodialysis catheter C into a functional position. However, if the practitioner is not able to cross the occluded vein, which is not uncommon, then the venous pathway is lost.

When the most desirable pathway is no longer available, the practitioner must find an alternative pathway. Commonly, when the right jugular approach is no longer available, the practitioner instead uses a left jugular or, less favorably, a subclavian approach. When above-the-waist approaches are no longer available, the practitioner may place a catheter C via a femoral vein. When a femoral approach is no longer available, a catheter can be placed directly into the inferior vena cava or through the liver. While such alternative placement approaches are possible, they are less desirable for a variety of reasons.

Finally, after a prolonged history of HD access with catheter C use, some patients lose all venous access options. When this occurs, if peritoneal dialysis is not possible, the loss of access options is fatal.

While it would be possible to maintain venous access indefinitely by simply leaving in place an HD catheter, this is not a good solution. First, because it passes through the skin, an HD catheter is associated with a higher risk of infection and death. Second, the intravenous large caliber of the HD catheter is more likely than a smaller catheter to create thrombosis and intimal hyperplasia. Third, patients greatly prefer not to have a bulky external catheter hub. In addition to discomfort, a partially external catheter restricts the patient's ability to bathe and to perform other activities that could cause infection.

Because catheter placement can become difficult or even impossible over time, there is a need to preserve access pathways safely for as long as necessary, potentially years. The invention provides a method and device to maintain catheter C access durably and safely in a patient who may need intermittent percutaneous catheter C placements, such as a patient undergoing hemodialysis (HD). The system includes an easily and quickly implantable catheter device 10 (see FIG. 1) that acts as a place keeper for a venous access pathway that otherwise may be lost over time. In addition to maintaining access, in embodiments, the device functions as a portacath.

SUMMARY OF THE INVENTION

To solve the above-mentioned problems, the present invention describes a method that permits a venous access pathway to be maintained indefinitely. The method consists of alternating between an internal/external hemodialysis catheter C, which is in place only while it is needed, and the fully implanted catheter device 10 of the invention. The implanted device remains in place when the patient has a functioning fistula or graft, acting primarily as a place keeper for a subsequent catheter C or other device placement. In embodiments, the implanted device may also be accessed for venous infusions or blood draws, functioning as a portacath.

The method is made practical by an implantable catheter device 10 of the invention, which is easily inserted over a guidewire 22 at the time of HD catheter C removal. When a dialysis catheter C is no longer needed, rather than the current standard practice of only removing the catheter C, the practitioner instead also implants the catheter device 10 of the invention to maintain a pathway for future use. If a HD catheter C is subsequently needed, the invention provides mechanisms to exchange the implanted catheter device 10 for a new HD catheter C.

The implanted catheter device 10 has no external component, so it does not limit patient activities and is much less likely to become infected. The distal portion intravenous segment 11 of the catheter device 10 has a much smaller caliber than an HD catheter, so there is less risk of thrombosis and hyperplasia. A primary advantage of the method and device is simplicity and speed of insertion, generally taking only 1-2 minutes when there are no pauses of activity progressing toward device insertion.

The catheter device 10 and all envisioned embodiments can be used in humans and animals such as those found on a farm, pigs, cows, horses, llamas, deer, etc. and those found as pets, cats, dogs, etc.

BRIEF DESCRIPTION OF THE DRAWINGS

In FIG. 2A, the detachable pusher device 60 is depicted as not yet attached to the catheter device 10, and the activating proximal back end, thumb rest 20, of the detachable pusher device 60 has not been depressed. The flange 14 is in the inactive state. The activating segment 14*a* is in the inactive position. The inner shaft 24 of the detachable pusher device 60 is shown having a screw configuration for attachment 25*a*.

FIG. 2B. The detachable pusher device 60 is detached from the catheter device 10, but the activating ring, or thumb rest 20, of the detachable pusher device 60 proximal back end has been depressed, which has advanced an activating segment 14*a* of the pusher forward.

FIG. 2D identifies the cross-sectional plane and point of view, arrow directional, for cross-sections 2E and 2F that are illustrated as FIG. 2E and FIG. 2F, respectively.

FIG. 4 shows a non-limiting method of exchanging an existing catheter C for a device 10 of the invention. Specifically, it shows a non-limiting method of how an existing catheter C could be removed over a guidewire, and how a catheter device 10 of the invention would be placed over the guidewire.

FIG. 5 shows a method of maintaining a venous access pathway after implantation of an implanted catheter device 10, wherein the implanted catheter device 10 is exchanged for a new catheter C in the patient P. This method demonstrates one potential mechanism and is non-limiting to permit the placement of a new hemodialysis catheter C using a path maintained by a catheter device 10 of the invention. A small incision Ia is made over the proximal subcutaneous hub 15, and methods, such as blunt dissection, are used to expose and to free the proximal subcutaneous hub 15 from the subcutaneous tissue (FIG. 5A). Similar to a primary tunneled catheter placement, a second small incision Ib is made below the proximal subcutaneous hub 15 and incision Ia or wound (FIG. 5B).

FIG. 5E and FIG. 5F depicts inserting a peel-away sheath 30 over the guidewire 22 in the vacated subcutaneous tract and inserting the new catheter C via the peel-away sheath 30 over the guidewire 22 and into the venous pathway. Once the path is large enough, a peel-away sheath 30 is advanced (FIG. 5E), and a new catheter C is placed via the peel-away sheath 30 (FIG. 5F). Passage of the new catheter C may be facilitated by a guidewire 22, such as a 0.035 inch stiff glide. Any incisions are optionally packed and closed.

FIG. 7. The catheter device 10 is depicted as having a luminal chamber 12*c* in the proximal subcutaneous hub 15. The luminal chamber 12*c* is shown as being continuous with the lumen 12 of the catheter device 10. The luminal chamber 12*c* comprising an inner diameter, a wall thickness of the proximal subcutaneous hub with the luminal chamber 51*a*, an access region of the proximal subcutaneous hub 52, and a wall thickness of the access region 51.

FIG. 7*d* identifies the transverse cross-sectional plane and point of view, arrow directional, for cross-sections that are illustrated as FIG. 7*e* and FIG. 7*f*, respectively.

The detachable pusher device 60 is illustrated having a "snout" 56, i.e., it is a configured element having a mechanism to displace the valve 17, such as a pointed hollowed cylinder as drawn, which allows the guidewire 22 and any fluid to move freely through the lumen 12.

DETAILED DESCRIPTION

Figure 1:
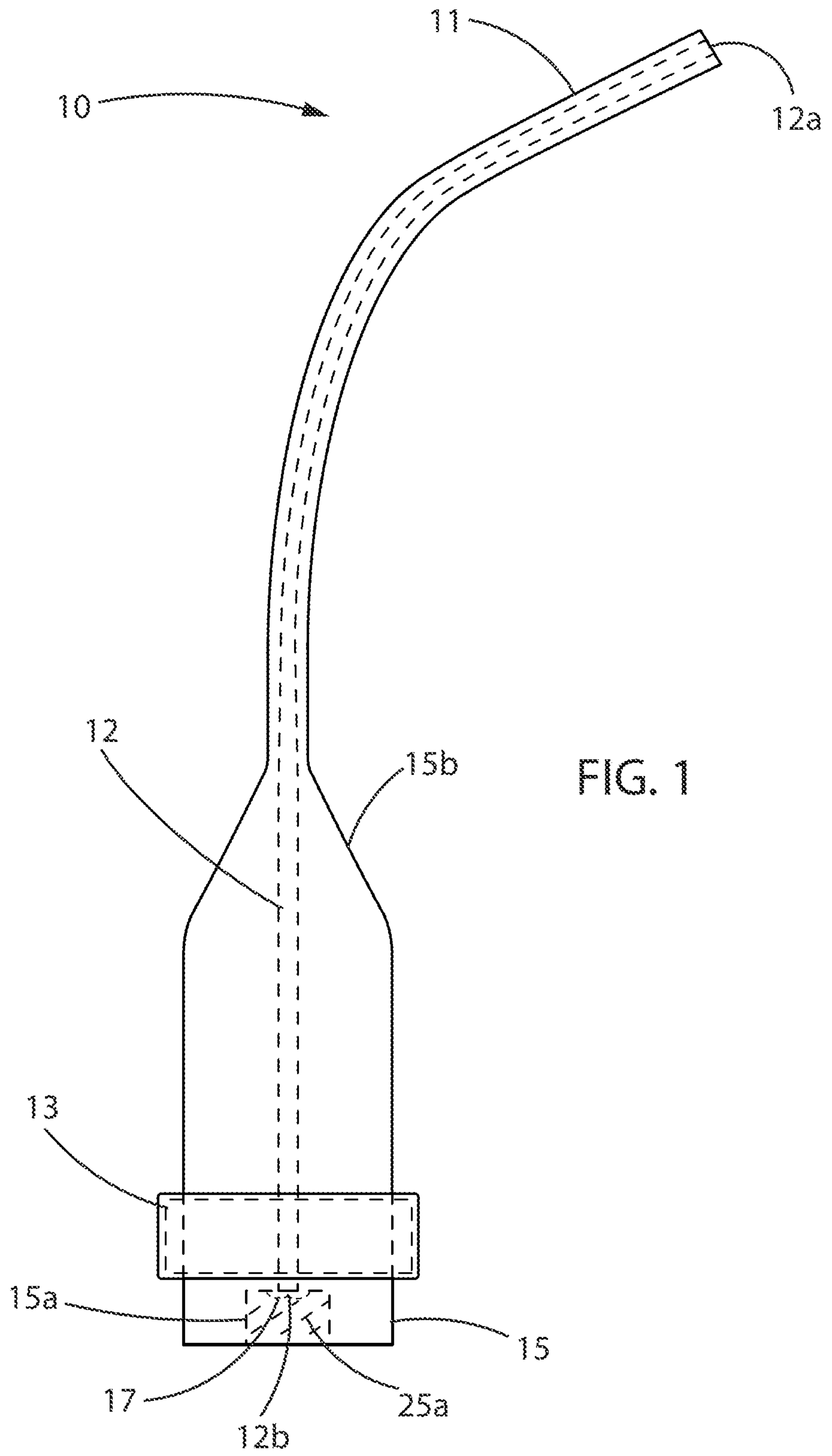
FIG. 1 is a non-limiting representative example of a schematic of the catheter device 10 of the invention. The catheter device 10 has a lumen 12 with openings of the lumen 12 having a front end opening of the lumen at the distal terminus 12*a* and at a back end opening of the lumen at the proximal terminus 12*b*. The back end (the proximal end) of the catheter device 10, or the proximal subcutaneous hub 15, has an outer diameter at least as large as a hemodialysis catheter C, typically 14 to 17 French, or up to 20 French, and potentially larger. The outer diameter of the catheter device can step down or preferably have a taper 15*b* to a smaller outer diameter of the distal portion 11, part of which is inserted into a luminal space, such as the venous system, as an intraluminal segment or, if the device is used for venous access, an intravenous segment. The outer diameter of the distal portion 11 can be as small as 2.5 French or 3 French, or 1 mm. The proximal subcutaneous hub 15 can have a configuration for attachment 15*a* at its proximal terminal portion. Not to be limiting, the configuration for attachment 15*a* is depicted as a screw configuration for attachment 25*a*. The subcutaneous hub can have a valve 17 (i.e., a mechanism to restrict flow of fluid through the lumen of the catheter device) such as a hemostatic valve. The proximal subcutaneous hub 15 is illustrated as having a retention cuff 13 as an anchoring system.
Figure 2A:
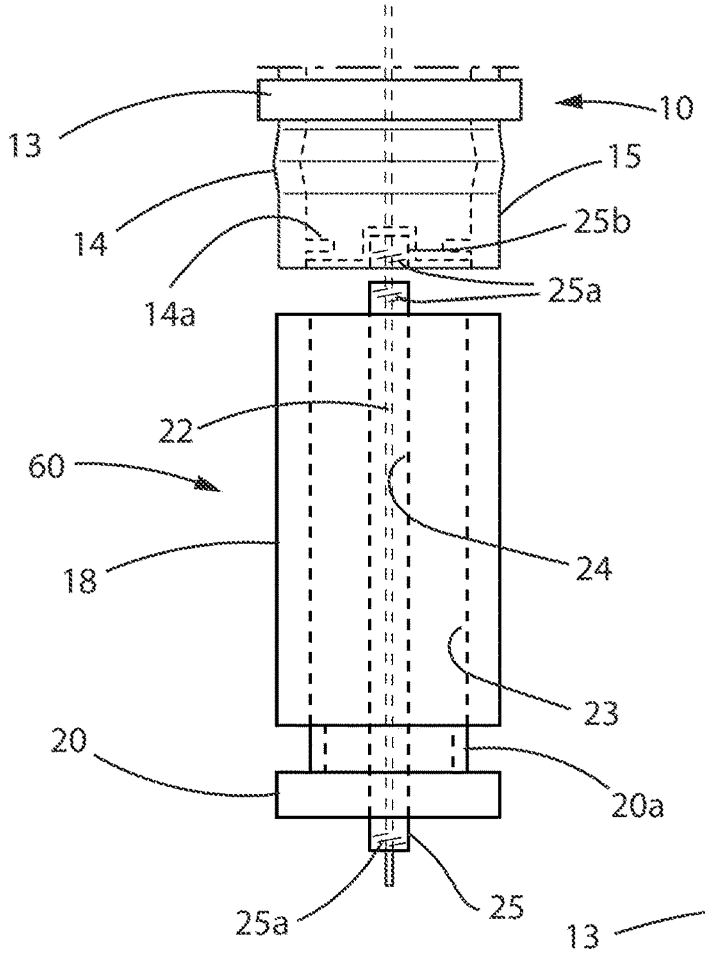
FIGS. 2A and 2B demonstrate a possible design for the detachable pusher device 60 and the back end of the catheter device 10 with a flange 14 of the retention system. The retention cuff 13 of the catheter device is shown in a relative position to the flange 14. The barrel of the detachable pusher device 18 has an internal wall of the barrel 23 that interfaces with an outer wall of the plunger 20*a*. The inner shaft 25 of the detachable pusher device interfaces the inner wall of the plunger 24 of the detachable pusher device 60. A guidewire 22 is depicted going through the lumen of the detachable pusher device 60 and the catheter device 10. The catheter device 10 depicts a receiving receptacle 25*b* showing the position of the inner shaft 25 of the detachable pusher device 60 engaging a screw configuration for attachment 25*a* (e.g., a screw configuration or luer lock) is depicted when the inner shaft 25 would be engaged with the screw configuration for attachment 25*a* of the catheter device 10.
Figure 2B:
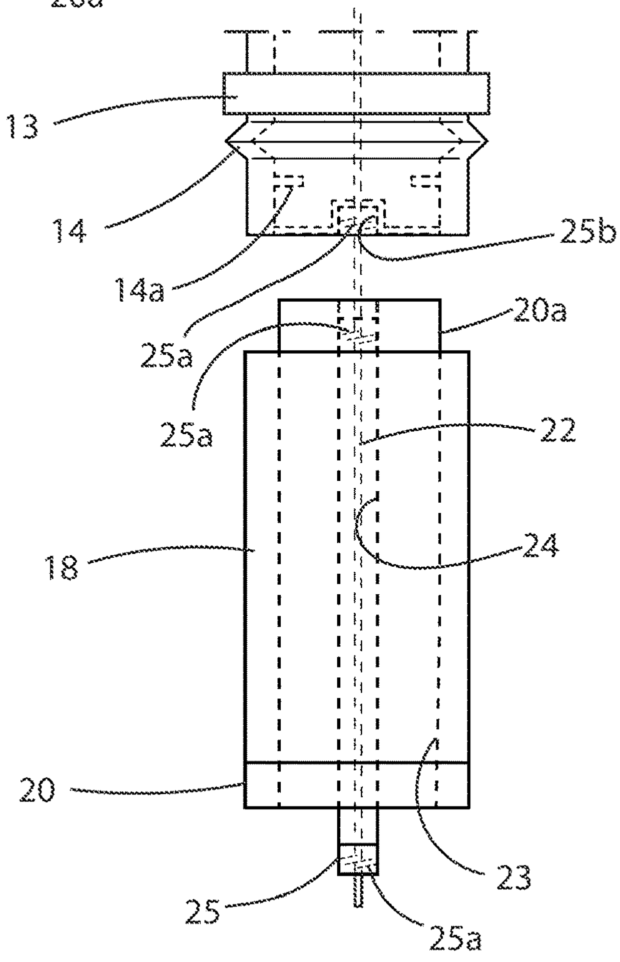
Figure 2C:
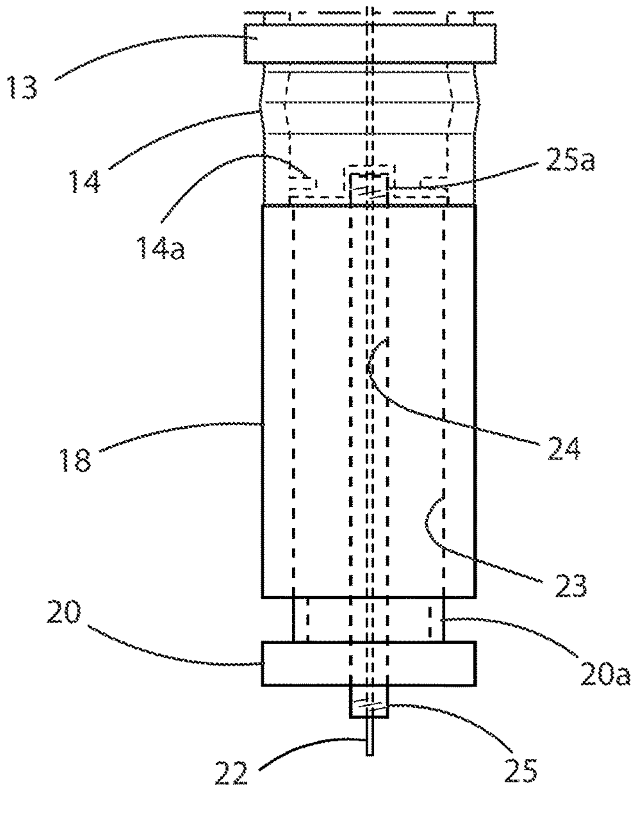
In FIG. 2C, the detachable pusher device 60 and the catheter device 10 are attached, as depicted by the configuration for attachment 25*a* of the inner shaft 25 engaging the receiving receptacle 25*b* of the proximal subcutaneous hub 15. But the activating back end of the detachable pusher device, thumb rest 20, has not been depressed.
Figure 2D:
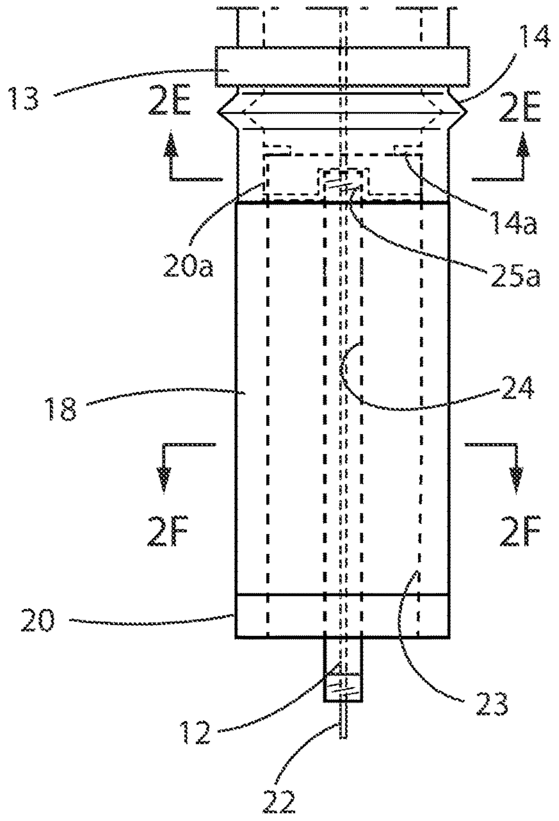
In FIG. 2D, the detachable pusher device 60 and the catheter device 10 are attached, and the activating back end of the pusher, thumb rest 20, has been depressed that resulted in an outward movement of the flange 14 at the proximal subcutaneous hub 15. The outer wall of the plunger 20*a* has been depicted as engaging the activating segment 14*a*.
Figure 2E:
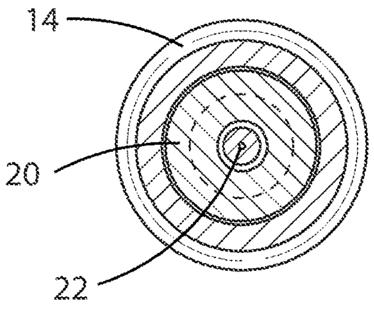
Figure 2F:
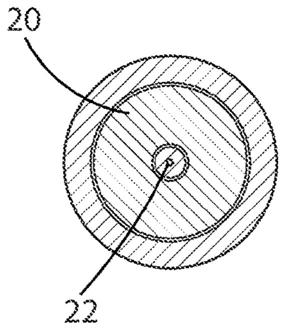

In FIG. 1 and FIG. 2, a catheter device 10 and a detachable pusher device 60 are attached through a quarter- or half-turn screw mechanism, which can be the screw configuration for attachment 25*a*, although many other attachment mechanisms are feasible, such as press fit held by tension. If there is an anchoring system in addition to the retention cuff 13, this may comprise a button or circumferential ring that, when depressed, causes the additional anchoring system of the retention system to flange outward, like the flange 14. The guidewire 22 could be between 0.0014 to 0.038 inch or have nominal size of about 0.014, about 0.018, about 0.035 or about 0.038 inch, although a 0.018 inch or smaller guidewire 22 would be most easily designed so that the intravenous segment of the distal portion 11 of the catheter device 10 could be made as small as 2.5 French.

Regarding FIG. 1, the proximal subcutaneous hub 15, has an outer diameter at least as large as a hemodialysis catheter C, typically 14 to 17 French. The diameter of the proximal subcutaneous hub 15 may be larger than the HD catheter C, or about 20 French, or even larger. A benefit of a larger hub 15 is that it would contribute more toward anchoring the catheter device. The catheter can step down or preferably have a smooth taper 15*b* to a smaller outer diameter distal portion 11, part of which is inserted into the venous system as an intravenous segment. The distal portion 11 preferably can be as small as 2.5 French or 3 French, or 1 mm. The distal portion can also be about 4 French, about 5 French, about 7 French, or about 8 French.

The proximal subcutaneous hub 15 may be considerably larger, in particular for the embodiments depicted in FIG. 7, about 30 French or more. In an embodiment, the preferred size of the outer diameter is about 30 French to about 36 French, or is about 30 French to about 40 French.

The term "about" is to allow for the tolerance of manufacturing within plus or minus (+) 2%, 3%, 5%, 8%, or 10% of the provided value.

The mechanism to prevent flow of fluid through the lumen 12 of the catheter device 10 prevents the direction of fluid from exiting the opening of the lumen at the proximal terminus 12*b* and comprises a valve 17 located within the lumen 12 of the catheter device, at the opening of the lumen at the proximal terminus 12*b* of the proximal subcutaneous hub 15, within the lumen 12 of the proximal subcutaneous hub 15, or a combination thereof.

In some embodiments, the luminal chamber 12*c* may have asymmetry, that is it may be offset from the axial center of the proximal subcutaneous hub 15 or lumen 12, wherein the wall thickness of the proximal subcutaneous hub with the luminal chamber 51*a* is located opposite of the wall from the access region 51 and wherein said wall thickness opposite of the wall from the access region 51*a* has a value greater than the wall thickness of the access region 51. The thicker region of said wall thickness opposite of the wall from the access region 51*a* may be of the same material of the bulk material of the proximal subcutaneous hub 15 or it may be comprising of other more rigid, harder, or denser material(s) to resist puncture from the insertion from the access region 52.

The wall thickness of the access region 51 can range from 0.25 mm to 1.0 mm, from 1.0 mm to 3.0 mm, or from 0.25 mm to about 3.0 mm. The wall thickness of the access region 51 can have nominal values where it is about 0.25 mm, is about 0.5 mm, is about 0.75 mm, is about 1.0 mm, is about 1.25 mm, is about 1.5 mm, is about 2.0 mm, is about 3.0 mm or is about 4.0 mm. The preferred wall thickness of the access region 51 is about 0.5 mm or ranges from 0.5 to 1.5 mm.

It is advantageous that the proximal subcutaneous hub 15 have features to help identify the orientation and the location of the access region 52. The proximal subcutaneous hub 15 may be shaped differently than what is shown in the figures. The proximal subcutaneous hub 15 may have a cross-sectional shape in the perpendicular plane of the lumen, identical to the orientation of the cross-section shown in FIG. 7*e*, where the cross-sectional shape is circular (as shown) but it may be also be oval, square, rhomboid, triangular, or asymmetrically shaped like a tear drop. The shape being asymmetrical will help to find the orientation of the proximal subcutaneous hub 15 when palpitated to help located the face of the access region 52. Pending on the placement of the cross-section, the cross-sectional shape of the proximal subcutaneous hub 15 may be generally the shape of a "U" or "D" having convex or concaved shape or a combination thereof to help locate and/or guide the location of the access region 52, like a funnel guiding the location.

If the shape of the proximal subcutaneous hub 15 is not circular, then the values for the outer diameter sizes refer to the widest portion of the hub portion of the proximal subcutaneous hub 15.

Figure 7D:
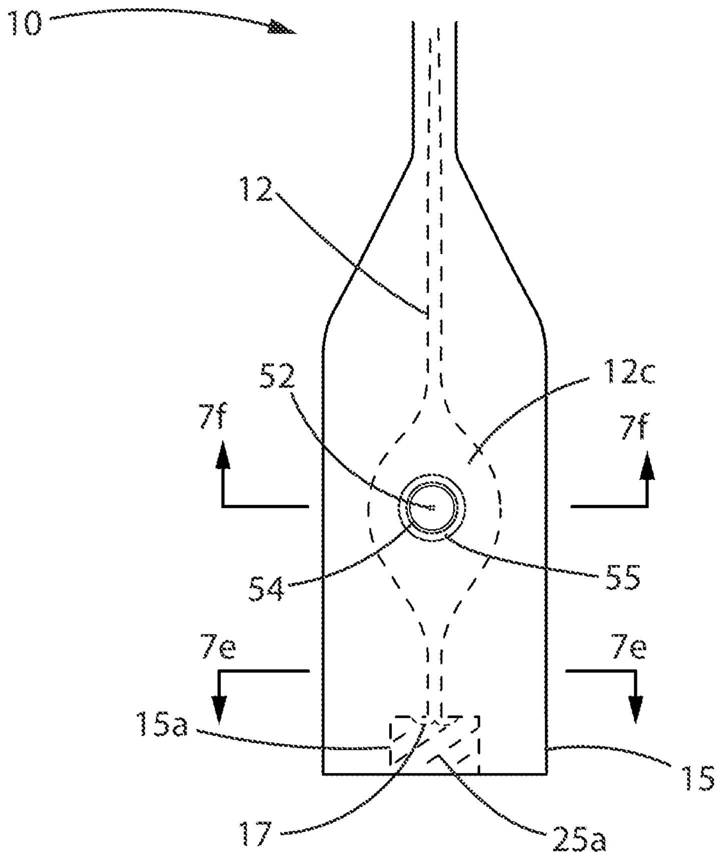
FIG. 7*d* further shows the needle access region 52 of the catheter device 10 comprising radiopaque markers or a radiopaque annular ring 55 surrounding the access region 52. The access region 52 is shown comprising a drum and/or self-sealing material whereby a needle N can puncture for access into the luminal chamber 12*c*. Since the luminal chamber 12*c* is a widened portion of the lumen 12, the needle is then in direct communication with the central veins via opening of the lumen at the distal terminus 12*a*.
Figure 7E:
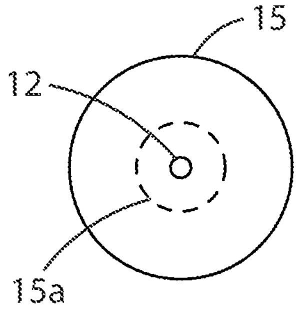
FIG. 7 shows a version of the catheter device 10 in which the proximal subcutaneous hub 15 of the catheter device 10 can be selected percutaneously with a needle N for intravenous infusions and/or blood sampling, with the catheter device 10 functioning like a portacath. In this version, the outer diameter of the proximal subcutaneous hub 15 may be larger than 17 French, and there is an access region 52 comprising a drum. The access region 52 can be accessed without incision via a needle N insertion through the skin after device implantation.
FIG. 7*a* identifies the transverse cross-sectional plane and point of view, arrow directional, for cross-sections 7*b* and 7*c* that are illustrated as FIG. 7*b* and FIG. 7*c*, respectively.
FIG. 7*g* is a cross-section representation along the medial coronal plane of an embodiment of the invention showing portions of the catheter device 10 and the detachable pusher device 60. The luminal chamber 50 is shown as a "bottle shape" having a less flared internal wall, at the proximal end of the luminal chamber 12*c*. The current illustration shows a valve 17 at the proximal terminus of the luminal chamber 12*c* but a portion of the lumen 12 can extend between the luminal chamber 12*c* and the valve 17.
Figure 7F:
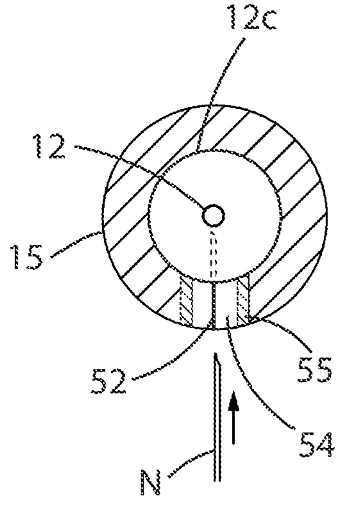
Figure 7G:
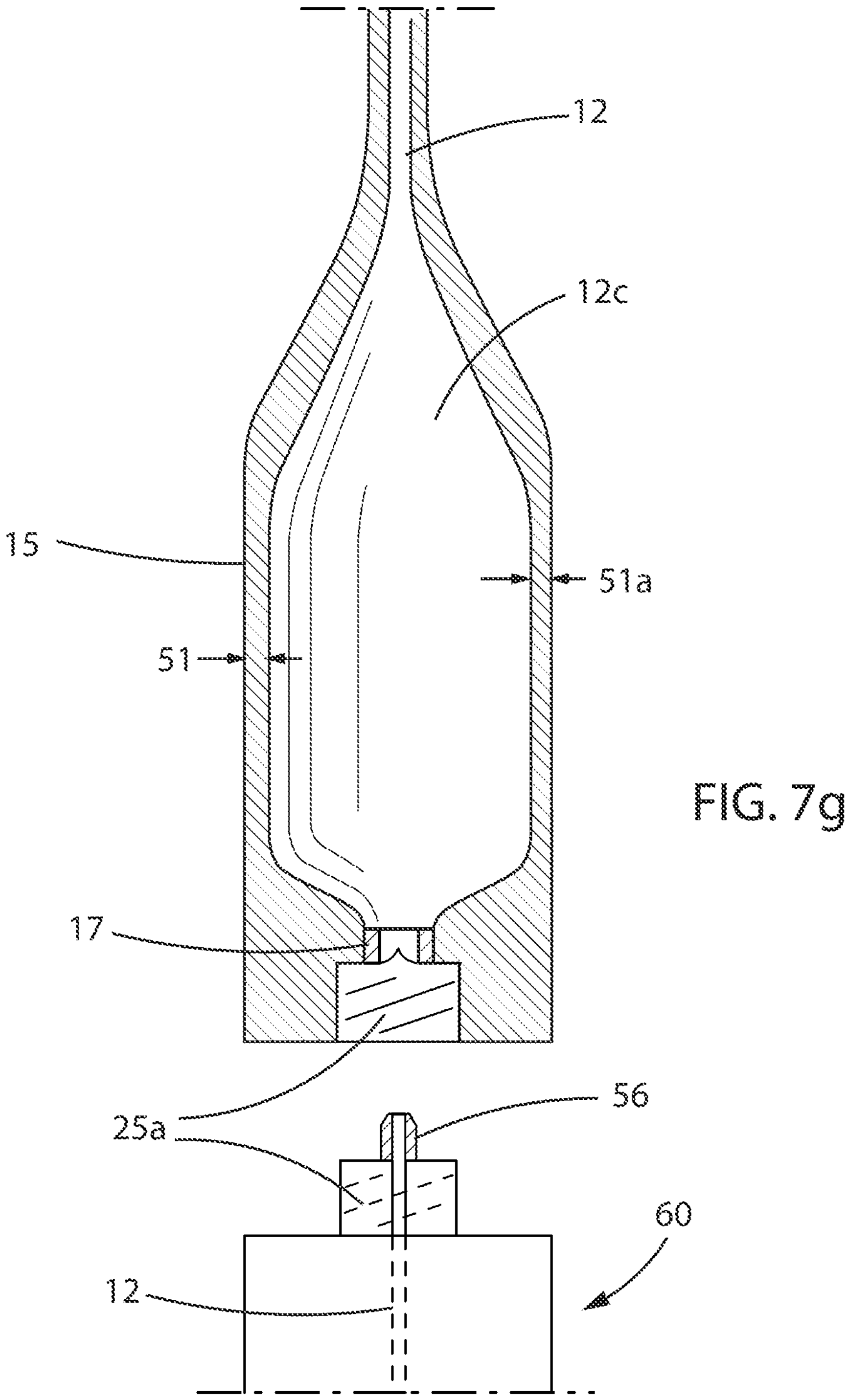

The wall thickness of the access region 51 and the wall thickness of the proximal subcutaneous hub with the luminal chamber 51*a* are shown in FIG. 7*g*, whereby each value can differ or be the same. If the wall thicknesses differ, this can result in radial asymmetry of the luminal chamber 50, it can result in asymmetry for the overall shape of the proximal subcutaneous hub 15, or it can result in generally no asymmetry in the overall shape for the luminal chamber 50 and the proximal subcutaneous hub 15 due to the change in thickness is localized to the space for the access region 52.

Figure 3A:
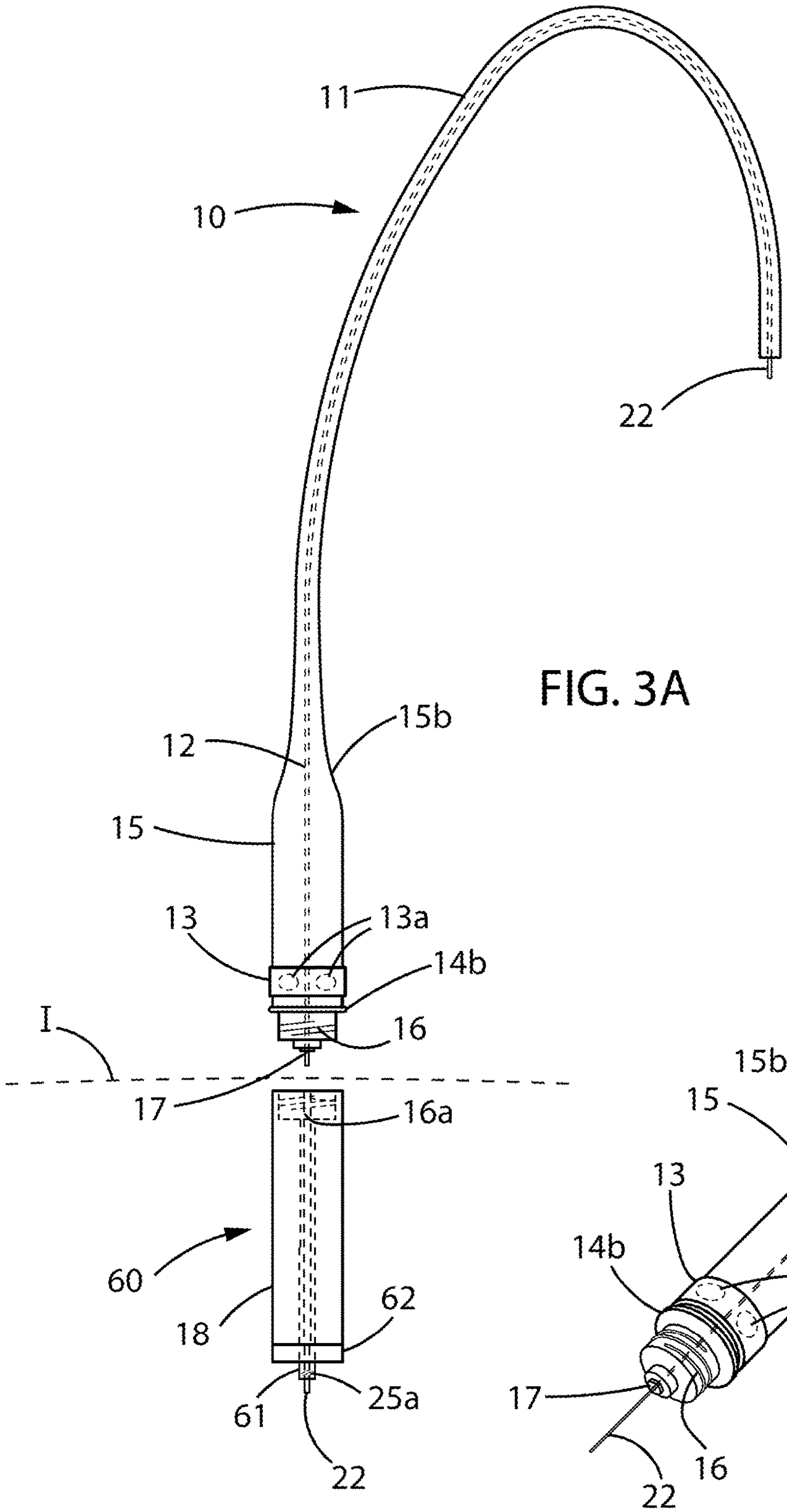
FIG. 3 is another variation of the detachable pusher device 60 and the catheter device 10 interface. In this version, the detachable pusher device 60 distal front end has a female screw configuration for attachment 16*a*, while the catheter device 10 proximal back end has a male screw configuration for attachment 16. The anchoring system in this version consists of a retention cuff 13 and shows a fixed flange 14*b*. Radiopaque markers 13*a* have been added to the catheter device 10 proximal back end. The valve 17 is illustrated at the opening of the proximal subcutaneous hub 15 of the catheter device 10. The guidewire 22 is shown through the lumen 12 of the detachable pusher device 60 and the catheter device 10. The taper 15*b* is shown in the catheter device 10. The relative location of the incision I is shown. The thumb rest 62 is shown with an appendage 61 having a type of a screw configuration for attachment 25*a*.
Figure 3B:
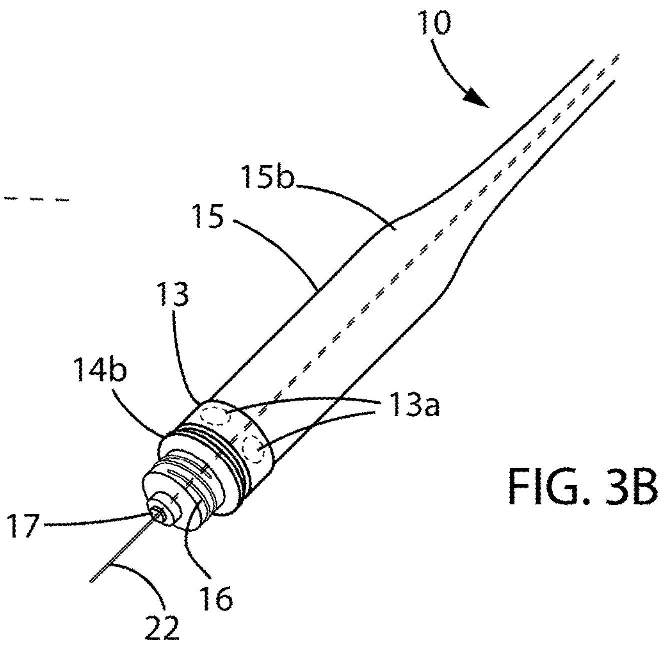
Figure 4A:
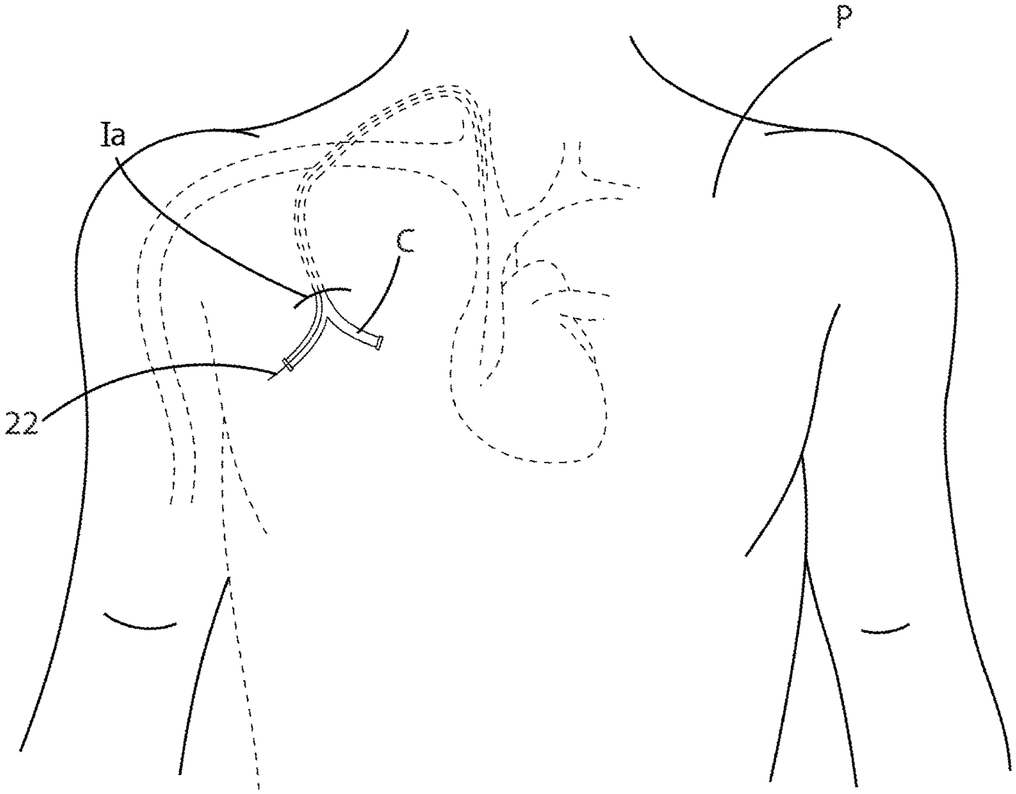
In FIG. 4A, a guidewire 22 has been established via the existing catheter C, extending into the central veins. The incision Ia is shown as the exit site of the catheter C.
Figure 4B:
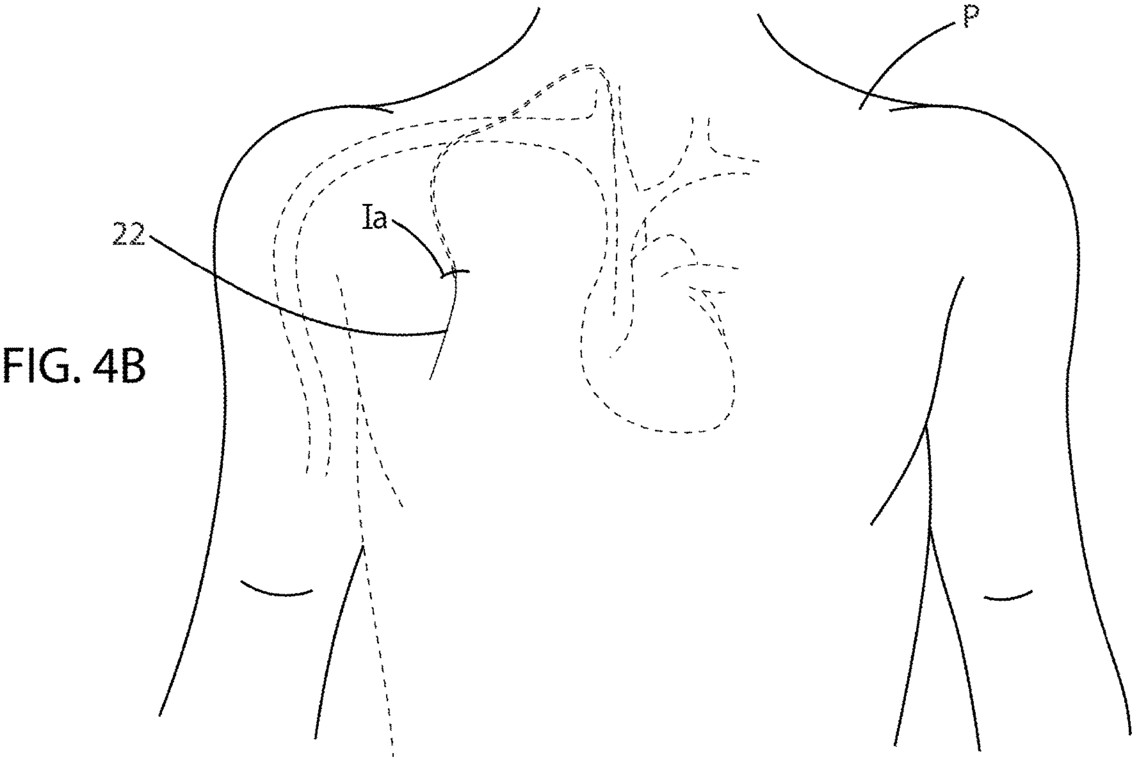
In FIG. 4B, the existing catheter C has been removed over the guidewire 22, leaving the guidewire 22 in place.
Figure 4C:
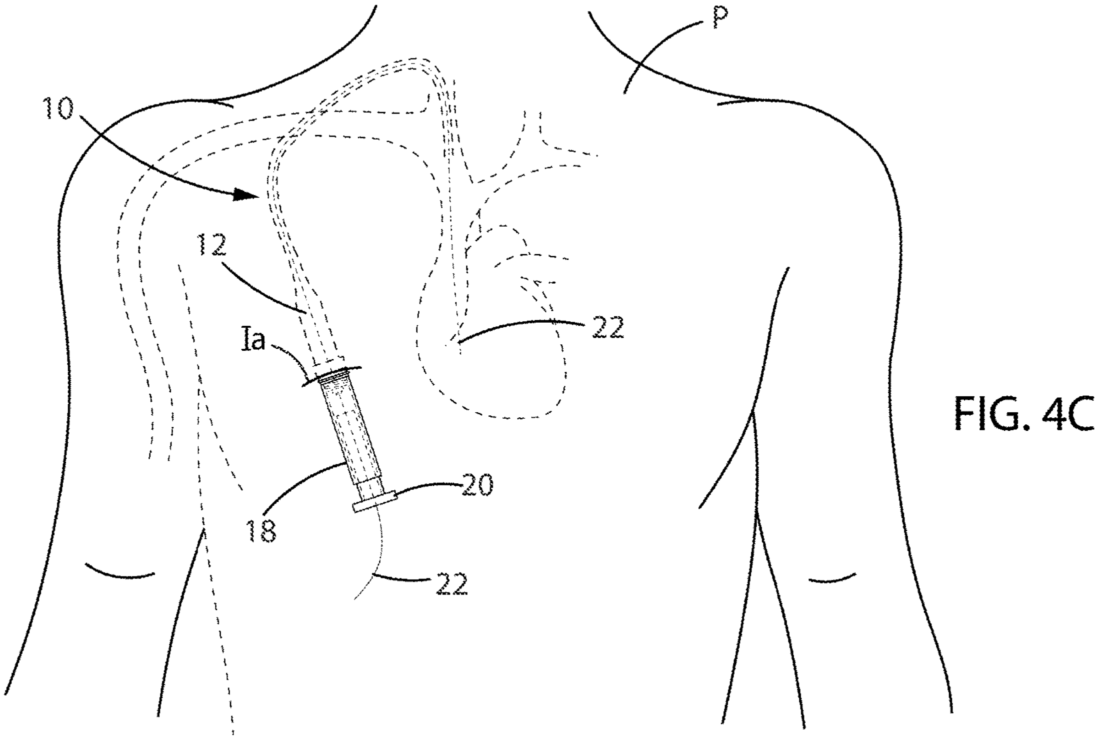
FIG. 4C, the catheter device 10 and the pusher 60 have been assembled, mounted on the guidewire, and delivered into the central veins. More specifically, assembly occurred by attaching a detachable pusher device 60 to the proximal subcutaneous hub 15 of the catheter device 10 of the invention, and advancing the assembly over the guidewire 22 using the pre-existing incision Ia or exit site from the catheter C. At this point, the guidewire 22 can be removed, and the catheter device 10 of the invention can be flushed via the detachable pusher device. Not shown here in FIG. 4C is the appendage 61 and a screw configuration for attachment 25*a* at the proximal face of the thumb rest 20 or thumb rest 62 that can be used to attach a syringe for flushing the assembled implantable catheter system.
Figure 4D:
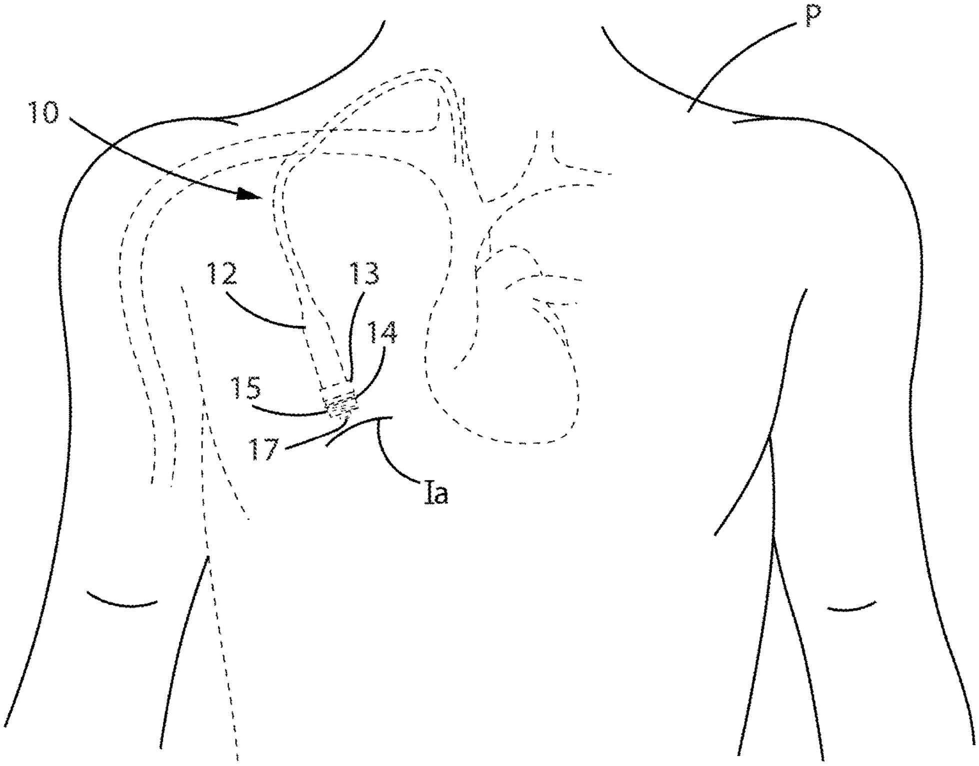
In FIG. 4D, disassembling the implantable catheter system and removing the detachable pusher device 60 from the catheter device 10 is shown whereby the detachable pusher device 60 has been detached from the catheter device 10 of the invention, which is now fully internal and any incision(s) or wound(s) can be packed or allowed to heal on their own by secondary intention.
Figure 5A:
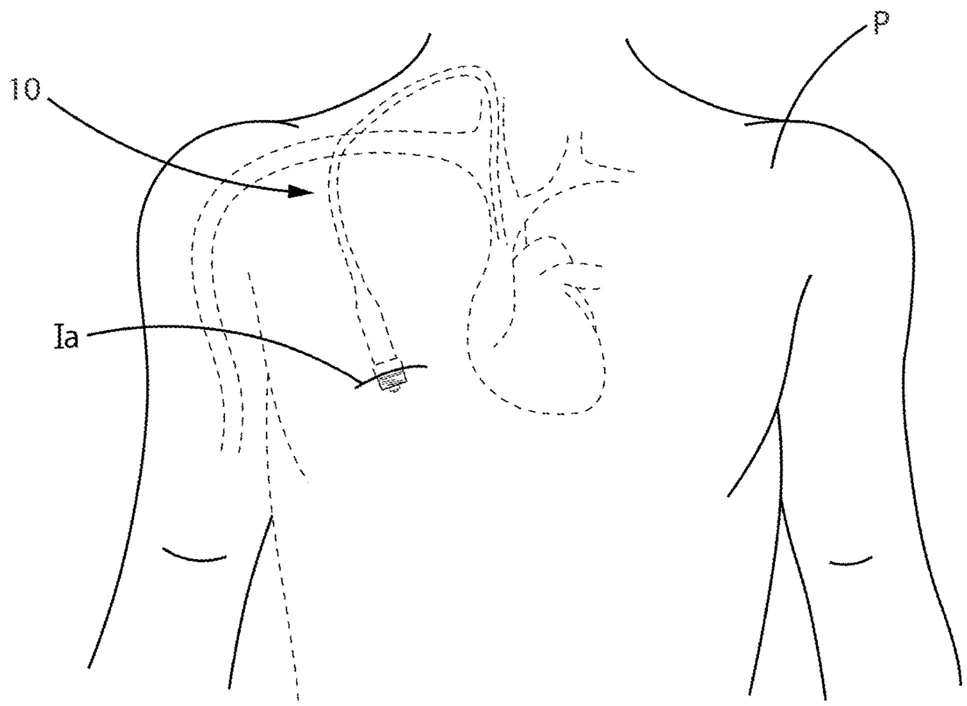
Figure 5B:
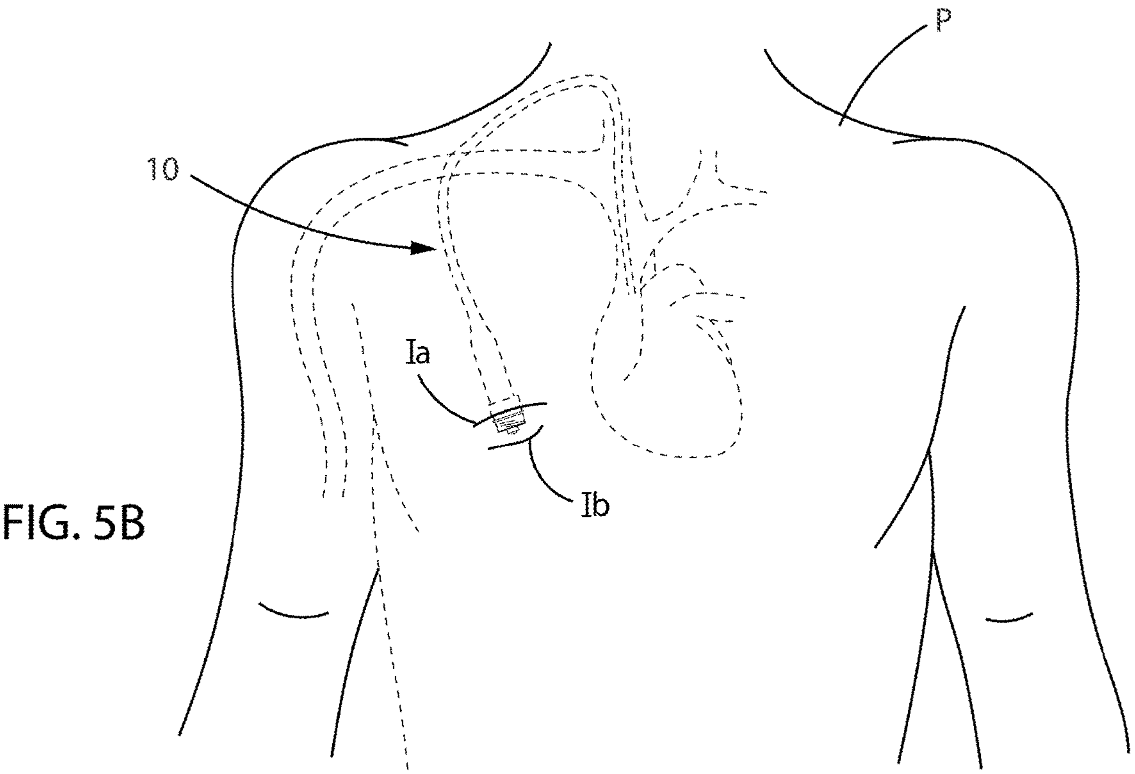
Figure 5C:
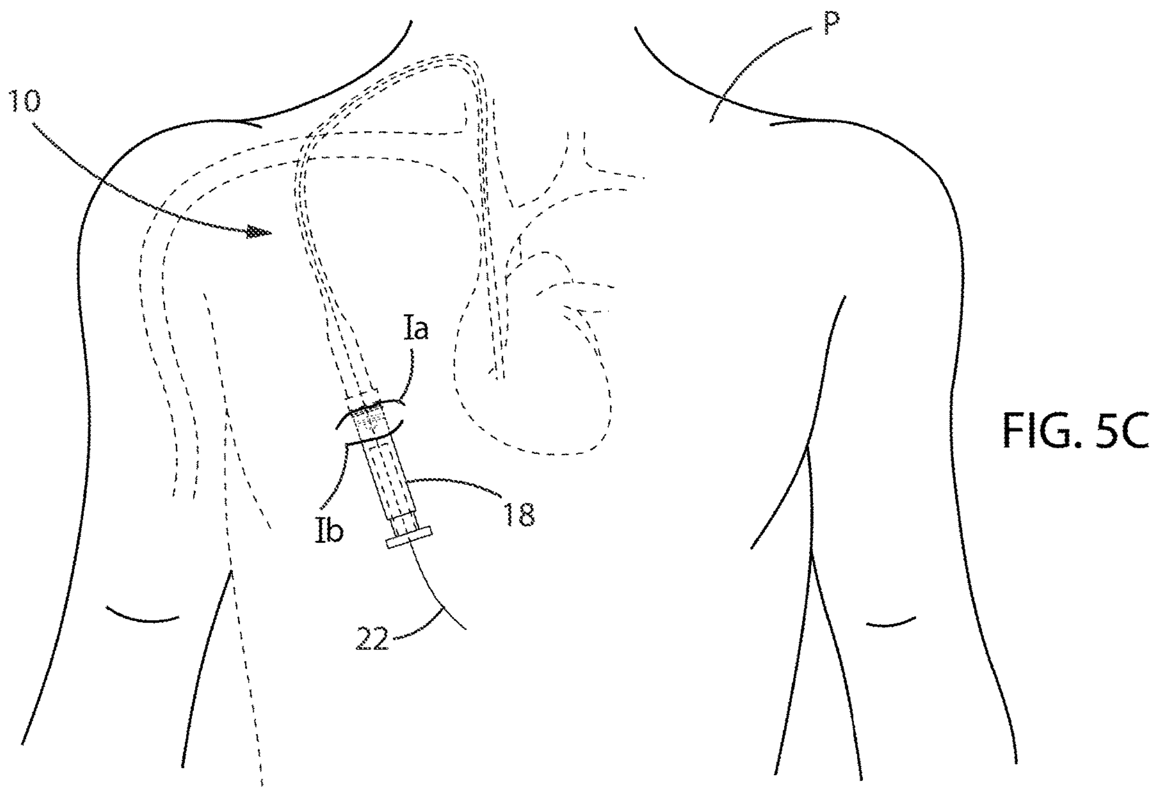
FIG. 5C depicts attaching the detachable pusher device 60 to the proximal subcutaneous hub 15 of the catheter device 10 to make the mated catheter system. A detachable pusher device is brought from the second incision Ib to the catheter proximal subcutaneous hub 15 (FIG. 5C). The catheter system 10 and the detachable pusher device 60 are assembled to make the mated catheter system by attaching the detachable pusher device 60 to the proximal subcutaneous hub 15 of the catheter device 10. When mated, the central lumen of the pusher 60 is aligned with the lumen 12 of the catheter device 10 back end opening 12*b*. This alignment of the lumen 12 permits a guidewire 22 to pass via the detachable pusher device 60 and through the catheter device 10. The guidewire 22 is then brought into the superior vena cava or deeper into the venous system.
Figure 5D:
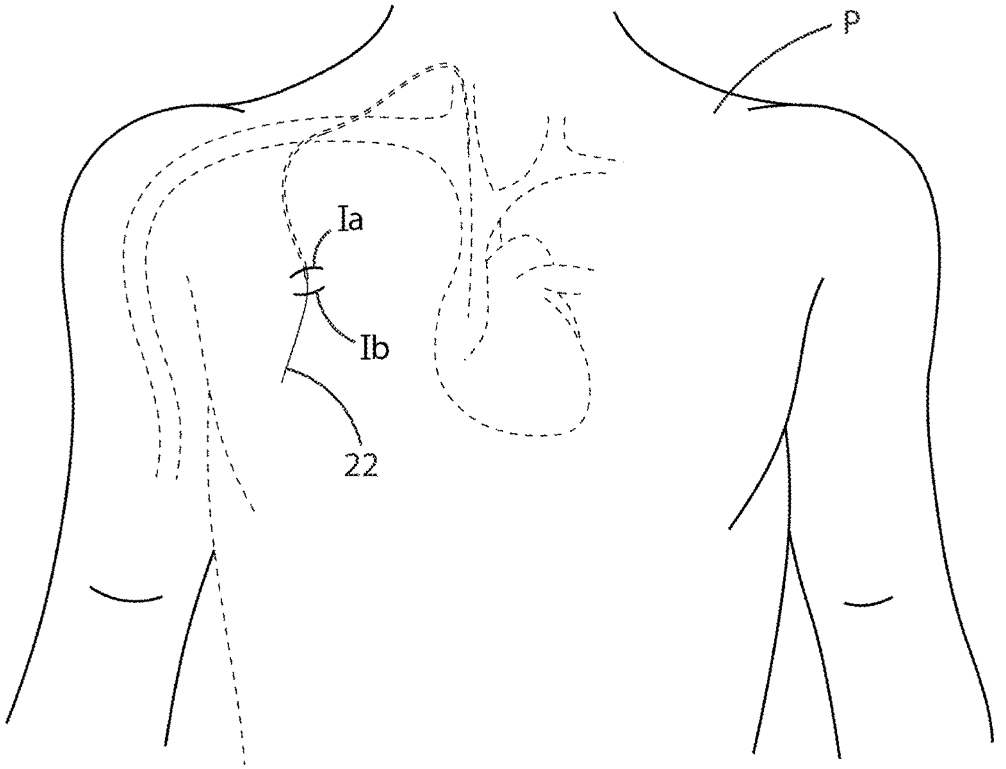
FIG. 5D depicts removing the mated catheter system over the guidewire 22 to produce a vacated subcutaneous tract and intravenous pathway traced by the guidewire 22. The mated catheter system is then removed from the patient P over the guidewire 22 while leaving the guidewire 22 in place (FIG. 5D).
Figure 5E:
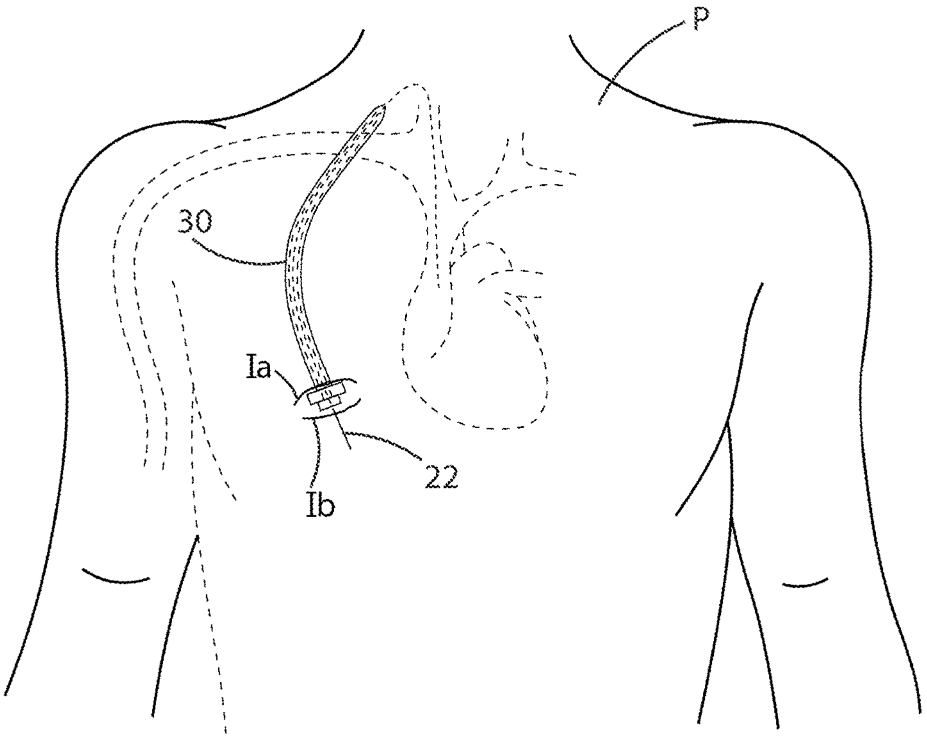
FIG. 5E depicts dilating the vacated subcutaneous tract and intravenous pathway traced by the guidewire 22. Once the mated catheter system is removed, the tract and central veins are dilated, either using a dilator, angioplasty or both techniques. It may be useful to upsize or enlarge the diameter or gauge of the guidewire 22 at that point using a coaxial catheter.
Figure 5F:
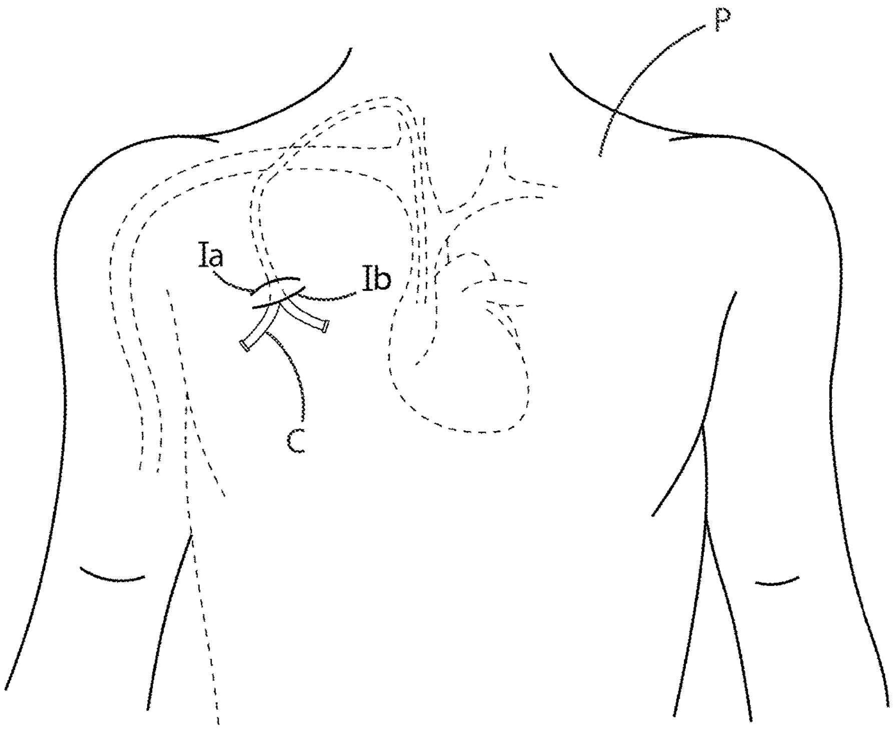

The device would be flushed, for example with a heparin solution prior to detachable pusher device 60 removal. The FIG. 1 design includes a screw configuration for attachment 25*a* preferably a luer lock at the proximal back end of the detachable pusher device 60, and the detachable pusher device 60 distal front end mates with the proximal back end of the catheter device 10 so that injection of fluid into the detachable pusher device 60 results in flushing of the assembled catheter device 10 with the detachable pusher device 60. As demonstrated in FIG. 1, FIG. 2 and FIG. 3, the male/female design can be reversed between the detachable pusher device 60 and the catheter device 10.

Figure 6A:
FIG. 6A and FIG. 6B shows an alternative approach illustrating a balloon catheter 40 in which the back end of the implanted catheter device 10 includes a balloon 42. Inflation of the balloon 42 creates a larger caliber back end that acts to achieve hemostasis by occluding the tract and which would also provide an anchoring mechanism of the retention system (FIG. 6B). The back end of the device could also include a retention cuff 13 and other features.
Figure 6B:
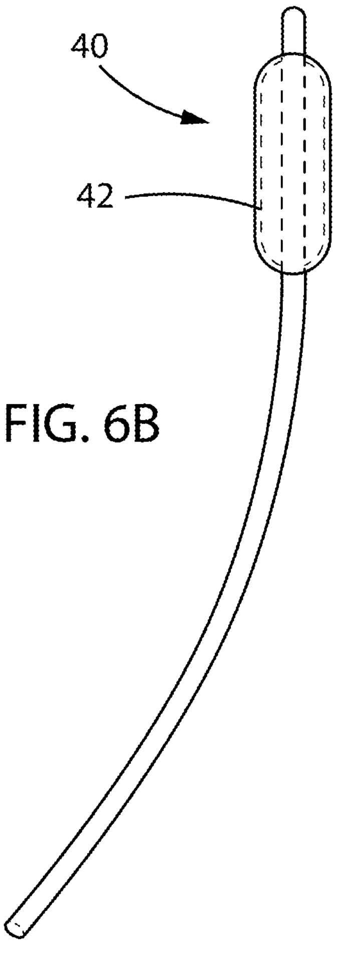

With respect to the anchoring device in addition to the retention cuff 13, the current invention demonstrates a possible approach and is a non-limiting example. There are many other possible anchoring systems, including the balloon 42 of FIG. 6. Further, it is possible that a device could be anchored by the retention cuff 13 alone, or some combination of anchoring mechanisms for the retention system.

With respect to the percutaneous needle-accessible device of FIG. 7, in the diagram, there are 2 hub components that permit access to the lumen 12, the guidewire 22 entry point opening at the proximal terminus 12*b*, and the aperture for needle entry at the access region 52, but there is only 1 lumen 12. In an embodiment this design is made functional by a hemostatic valve 17 near the guidewire 22 insertion port at the back end of the proximal subcutaneous hub, opening of the lumen at the proximal terminus 12*b* of the catheter device 10. When the detachable pusher device 60 is mated with this port, the valve 17 is opened by the snout 56 of the detachable pusher device 60, so that the lumen 12 can be flushed via the detachable pusher device 60. When the detachable pusher device 60 is detached from the proximal subcutaneous hub 15, the valve 17 shuts, closing the lumen 12 of the catheter device 10 from the surrounding soft tissues. Subsequently, if the catheter device 10 is percutaneously accessed via the drum 54 covered access region 52, or side-aperture, aspiration and flushing of the catheter device 10 would only draw and flush via the opening of the lumen at the distal terminus 12*a*, since the opposite back end opening of the lumen at the proximal terminus 12*b* is sealed by the valve 17, such as the preferred hemostatic valve.

The proximal subcutaneous hub 15 and the luminal chamber 12*c* of FIG. 7 may not be perfectly cylindrical. Externally, a portion or portions of the proximal subcutaneous hub 15 may be flattened to decrease the anterior/posterior dimension after placement in order to decrease the risk of flipping. Internally, the luminal chamber 12*c*, the port or access region 52 may have a flattened harder wall opposite the side aperture so that needles placed through the aperture, access region 52 cannot puncture the opposite wall at the time of needle access.

In an embodiment, the device of FIG. 7 may also have additional markers to facilitate fluoroscopic-guided needle access for use. In particular, there can be a radiopaque annular ring 55 around the access region 52 or side-aperture. Also, a marker or markers, such as radiopaque markers 13*a*, may be placed on the side opposite the side-aperture, for example at the center of the side opposite the aperture. A practitioner accessing the device chamber using fluoroscopic guidance could then rotate an image intensifier to position the opposite-side marker, or radiopaque marker 13*a*, within the radiopaque annular ring marker 55, then place the needle through the radiopaque annular ring 55 until it hits the opposite marker or radiopaque marker 13*a*. Additionally, radiopaque markers 13*a* could be asymmetrically placed near the radiopaque annular ring 55, such as to the right or to the left, so that visualizing the posterior vs anterior orientation of the access region 52 can be identified.

With respect to the risk of infection, while the device in embodiments is placed via an existing tract that is assumed to be colonized by bacteria, device infection should be prevented by an antimicrobial barrier in the proximal subcutaneous hub 15 of the device or adjacent to it. Risk of infection would also be limited by administration of an antibiotic one hour before catheter exchange, which is already common practice. Further device infection risk reduction could be achieved through a longer course of antibiosis after placement, and possibly through the temporary packing of the wound with iodophor gauze or the equivalent. The antiseptic may be delivered through the detachable pusher device 60 at the time of removal. Over the longer-term, because the catheter device 10 of the invention is fully implanted, it should have a very low rate of infection, like that of a pacemaker.

Another mechanism to decrease infection risk is that the catheter device 10 can, in an embodiment, be placed through a peel-away sheath 30. Once an existing HD catheter Cis removed over a guidewire 22, and once the tract has been dilated, a peel-away sheath 30 is inserted. This both facilitates passage of the detachable pusher device and catheter device 10 of the invention and also acts as a sterile conduit through which the device is placed. The peel-away sheath 30 is removed immediately after device delivery. Since the invention device is shielded from the chest wound by the peel-away sheath 30, the device would not be seeded at the time of insertion.

With respect to anchoring of the catheter device 10 at the time of implantation, if there is a retention cuff, another option would be to leave the detachable pusher device 60 in place for a period of weeks, such as two weeks, three weeks, four weeks, five weeks, six weeks, or seven weeks or eight weeks, until the retention cuff 13 is affixed to the body of the patient P, such as to the chest wall. As an example, after 4-6 weeks, the retention cuff 13 could be tested for stability, and the detachable pusher device 60 would be removed. The practitioner may use iodophor gauze or the equivalent at the time of detachable pusher device 60 removal. Such a delay in detachable pusher device 60 removal would not be necessary if the subcutaneous tract is sufficiently long, and if there is adequate restriction to movement at the time of device placement. Alternatively, if there is an anchoring system in addition to the retention cuff 13, as described herein, then the delayed detachable pusher device 60 removal would also not be necessary.

Regarding the proposed mechanism to insert a new HD catheter C in FIG. 5, there are other possible ways to place an HD catheter C via the invention. Another possible mechanism would be to make a small incision Ib below the proximal subcutaneous hub 15 position, then to approach the invention proximal subcutaneous hub 15 with a needle that could be inserted into the proximal back end of the catheter device 10 into the opening of the lumen at the proximal termini 12*b*. A guidewire 22 could then be advanced through the needle and through the catheter device 10 through the lumen 12. Once the guidewire 22 is established in the venous system, such as the superior vena cava (SVC) or deeper, the produced vacated subcutaneous tract and intravenous pathway traced by the guidewire 22 could be dilated via some combination of dilators and/or angioplasty, then the new catheter C could be placed through a peel-away sheath 30. Using this technique, it may be possible to perform only one small incision Ib below the implanted catheter device 10. This may require that the retention cuff 13 or other anchoring system is locate near enough to the incision Ib to free it.

With respect to the material used in the intravenous segment of the distal portion 11 of the implanted device, it is well-known in the art that certain materials and coatings are more favorable, with sufficient flexibility to take tight curves but with sufficient strength to prevent breakage during a firm withdrawal. Further, certain coatings can be applied to a catheter to prevent it from becoming stuck over time and to make catheter infection less likely. Additionally, an embodiment of the device of the invention includes radiopaque markers for fluoroscopic visualization at the time of device implantation, retrieval or exchange for a new HD catheter.

In an embodiment of the invention, while the proposed implanted device would most favorably taper from the hub to the intravenous portion, the amount of taper is arbitrary. It is possible that there is a step reduction in size, which could help to keep the proximal subcutaneous hub 15 in place. The key concept in the tapering is that the proximal back end should be large enough to contribute to position fixation and hemostasis, while the distal front end should be small enough to minimize intravenous thrombosis and intimal hyperplasia. Since the catheter device 10 is not used for dialysis, there can be a single lumen 12, and, in embodiments, the inner diameter of the lumen 12 can be as small 0.014 inch, or in the range from 0.014 inches to about 0.044 inches, or is about 0.018 to about 0.035 inches. As in FIG. 6, a taper 15*b* could also be achieved by incorporating a balloon at the proximal back end, such as around the proximal subcutaneous hub 15. At a time when the catheter device 10 is to be exchanged for a catheter C, such as a hemodialysis catheter, the vacated subcutaneous tract and intravenous pathway can be increased in size, as necessary, through the use of dilators, angioplasty, or a combination of dilators and angioplasty.

With respect to prior art, there are already devices on the market, such as standard surgical portacaths, that are fully implanted and that consist of a subcutaneous port and central catheter. In these standard portacath kits, the port and catheter are usually separate components that are connected toward the end of implantation. Such existing devices can be used to maintain a venous access pathway. However, this is rarely done. A principal reason is that a standard portacath requires a complicated and time-consuming process, which includes creating separate larger incisions, blunt dissection, and re-tunneling. For this reason, implantation of a portacath in this setting would take approximately 20-30 minutes or longer, while implantation of the invention catheter would take roughly 1-3 minutes, whereby the activity of implantation does not include any pause, i.e., that is all steps are being performed with movable action progressing to the next actionable step.

In an embodiment shown in FIG. 7, the invention catheter is modified so that it can be accessed percutaneously, like a portacath. In this embodiment, the proximal subcutaneous hub 15 is made larger, and there is a membrane-covered aperture, or drum, for needle insertion. In this embodiment, the proximal subcutaneous hub 15 may be considerably larger, about 30 French, about 35 French, about 40 French, about 45 French, about 55 French, about 60 French, 70 French, or larger to accompany the luminal chamber 50. In an embodiment, the preferred size of the outer diameter is approximately 30 French or 42 French, or between 10 and 14 mm. The catheter can step down or preferably have a taper **15*b* to a smaller outer diameter distal portion 11, part of which is inserted into the venous system as an intravenous segment. The distal portion 11 of any disclosed embodiment can be as small as 2.5 French or 3 French, or 1 mm. The distal portion 11** can also be about 4 French, about 5 French, about 7 French, or about 8 French.

In an embodiment shown in FIG. 7, the catheter device could be placed in a different fashion. Because this is a larger device, with a hub that is both wider and longer than other embodiments, and because the device is designed to function like a portacath, there will be circumstances when the device would be better implanted using a separate tunnel. A common circumstance for requiring a separate tunnel would be if the original HD catheter, for which the FIG. 7 embodiment of the device 10 is being exchanged, had a tunneled segment less than 5-6 cm below the clavicle.

If there is a need for a separate tunnel at the time of exchange from and HD catheter to the device of the invention 10, then this is a non-limiting possible sequence of steps for implantation: (1) After lidocaine infiltration, make a small incision over a cranial segment of the existing catheter C, freeing the catheter C. (2) Cut the catheter, then advance a guidewire 22 through the cranial portion into the central veins. Remove the back end of the existing catheter. (3) After lidocaine infiltration, make about a 1.5 cm incision approximately 4-5 cm below the clavicle, adjacent to but distinct from the exit site of the original catheter C. (4) Tunnel a device from the chest wound to the cranial incision, and then deliver the back end of the guidewire 22 from the venotomy to the new chest wound. (5) Over the guidewire 22, dilate (at about 6-8 French) the tract and venotomy, using this step to measure the length of the catheter for insertion. (6) Dilate the subcutaneous tissues using additional short dilators (length approximately 4 cm, diameters up to 30-40 French), creating a pocket for the port segment that is slightly smaller than the port itself. (7) Advance the portacath, catheter device 10, of the invention over the guidewire 22 into position, the port in the subcutaneous tissues and the catheter device 10 within the central veins. (8) Remove the guidewire 22 and flush the port via the guidewire portal. (9) Close the cranial incision, which may be accomplished with 1 or 2 stitches, a Steri-strip, Dermabond, or some combination. (10) Close the new chest incision, which may be accomplished with one subcutaneous buried resorbable suture, a Steri-Strip, Dermabond, or some combination. The old chest wound is allowed to heal by secondary intention.

In an embodiment shown in FIG. 7, the device could also be placed de novo primarily to function as a portacath. This is a non-limiting possible sequence of steps for implantation: (1) After lidocaine infiltration, make a small incision over a vein for access, usually the right internal jugular vein. (2) Select the vein via the incision using a needle, usually done using ultrasound guidance, and then pass a guidewire 22 through the needle into the central veins. (Some practitioners would access the vein first, then make the incision second.) (3) After lidocaine infiltration, make a 1.5 cm incision approximately 4-5 cm below the clavicle. (4) Tunnel a device from the chest wound to the venotomy, and then deliver the back end of the guidewire 22 from the venotomy to the chest wound. (5) Over the guidewire 22, dilate (at about 6-8 French) the tract and venotomy, using this step to measure the length of the catheter for insertion. (6) Dilate the subcutaneous tissues using additional short dilators (length approximately 4 cm, diameters up to 30-40 French), creating a pocket for the port segment that is slightly smaller than the port itself. (7) Advance the portacath, catheter device 10, of the invention over the guidewire 22 into position, the port in the subcutaneous tissues and the catheter device 10 within the central veins. (8) Remove the guidewire 22 and flush the port via the guidewire portal. (9) Close the neck incision, which may be accomplished with 1 or 2 stitches, a Steri-strip, Dermabond, or some combination. (10) Close the chest incision, which may be accomplished with one subcutaneous buried resorbable suture, a Steri-Strip, Dermabond, or some combination.

In the discussion below, the "long-axis" of the catheter device refers to the path of the lumen 12. The cross-section refers to planes orthogonal to the lumen 12.

In an embodiment of the catheter device depicted in FIG. 7, the access region 52 is accessed through the skin with a needle N, so it is important that the aperture or access region 52 remain oriented toward the skin. In order to avoid rotation around the long-axis, the proximal subcutaneous hub 15 may include flat wings extending from the front (distal) or back (proximal) of the proximal subcutaneous hub 15, but in a fashion that does not obstruct the ability of the detachable pusher device to assemble with the catheter device 10, as could be achieved if the proximal wings had a rocket fin-like configuration. There could be a single wing, or there could be 2 wings, three wings, or four wings or more wings, preferably, and for example, forming an "X" shape or stellate shape in the cross-section when there are four wings. In the long axis of the catheter device, the wings could extend 1 or 2 cm in front of the proximal subcutaneous hub 15. If extending from the front of the hub, the wings would replace the taper **15*b*** described above.

Stabilizing the port and preventing rotation could also be achieved via incorporating expanding wings. These wings could be either plastic, Nitinol, or some other material that can expand to assume an expanded shape when unconstrained. If the portacath embodiment of the invention catheter device uses self-expanding wings or struts, then delivery could include the use of a peel-away sheath. Specifically, the port hub would be positioned in the soft tissues through a peel-away sheath, which would constrain any self-expanding wings. Removal of the sheath would leave the self-expanding wings unconstrained, and the wings would therefore spring open.

At the time of portacath removal, the expanded wings could be re-constrained in a fashion similar to mechanisms used to retrieve an inferior vena cava filter, wherein a central spot at the front (near 12A) or the back of the port hub (near 12B) is grabbed and pulled while an open cylindrical device is advanced over the port hub. In this fashion, the self-expanding wings of the portacath embodiment of the catheter device would be forced back into the original constrained position, and the port would be removed.

The concept of a port segment with a roughly circular cross-section that uses wings to stabilize the port and prevent rotation has advantages even for conventional portacaths that are not designed for over-the-wire insertion. One of the time-saving features of the portacath device of the invention is the use of dilators rather than blunt dissection to fashion a pocket for the port. A second time-saving feature and source of cosmetic benefit is that incisions are smaller. These benefits arise from the mostly cylindrical shape, in particular the mostly circular cross-section, of the port portion of the proximal subcutaneous hub 15. These features, along with the wings to inhibit rotation, could be incorporated into a standard portacath.

To clarify, a standard port relies on a broad flat base to inhibit device flipping. Some practitioners suture ports to the chest wall to further prevent flipping. The drum, used for access, is smaller than the flat base. Therefore, it is the base of the port that necessitates a long incision. Contrariwise, the device of the invention does not require a broad flat base, instead relying on wings to prevent device rotation in the pocket. This permits the port to be inserted through a much smaller incision. Further, the roughly circular cross-section also enhances the use of simple dilators to create a pocket for the port during implantation, which requires less time and skill than blunt dissection.

There are many possible designs that incorporate a roughly circular port cross section plus rigid or self-expanding wings. In a preferred embodiment, the port segment is roughly cylindrical, with a roughly circular cross-section. This design is advantageous for an over-the-wire device of the invention. However, if incorporated into a standard portacath, the port segment could be spherical, ovoid, or any more complex shape that results in a roughly circular cross-section.

If a standard non-over-the-wire portacath were to use the cylindrical body with wings design, as described here in this work, for conversion of an existing catheter to a portacath, then a non-limiting possible sequence of insertion could be as follows: (1) After lidocaine infiltration, make a small incision over a cranial segment of the existing catheter C, freeing the catheter C. (2) Cut the catheter, then advance a guidewire 22 through the cranial portion into the central veins. Remove the back end of the existing catheter. (3) After lidocaine infiltration, make about a 1.5 cm incision approximately 4-6 cm below the clavicle, adjacent to but distinct from the exit site of the original catheter C. (4) Tunnel a grabber device or other mechanism from the chest wound to the cranial incision, and then deliver the back end of the guidewire 22 from the venotomy to the new chest wound. (5) Over the guidewire 22, dilate (at about 6-8 French) the tract and venotomy, using this step to measure the length of the catheter for insertion. (6) Dilate the subcutaneous tissues using additional short dilators (length approximately 4 cm, diameters up to 30-40 French), creating a pocket for the port segment that may be slightly smaller than the port itself. (7) Advance the separate catheter of the standard portacath system over the guidewire 22 into position, then remove the guidewire 22. Attach the hub/port, proximal subcutaneous hub 15, to the catheter. Advance the mated port and catheter until the port is in the subcutaneous tissues and the catheter further within the central veins. (8) Access the port with a Huber needle and flush the port. (9) Close the cranial incision, which may be accomplished with 1 or 2 stitches, a Steri-strip, Dermabond, or some combination. (10) Close the new chest incision, which may be accomplished with one subcutaneous buried resorbable suture, a Steri-Strip, Dermabond, or some combination. The old chest wound is allowed to heal by secondary intention.

If a standard non-over-the-wire portacath were to use the cylindrical body with wings design for a de novo placement of a portacath, then a non-limiting possible sequence of insertion could be as follows: (1) After lidocaine infiltration, make a small incision over a vein for access, usually the right internal jugular vein. (2) Select the vein via the incision using a needle, usually done using ultrasound guidance, and then pass a guidewire 22 through the needle into the central veins. (3) After lidocaine infiltration, make about a 1.5 cm incision approximately 4-6 cm below the clavicle, adjacent to but distinct from the exit site of the original catheter C. (4) Tunnel a grabber device or other mechanism from the chest wound to the cranial incision, and then deliver the back end of the guidewire 22 from the venotomy to the new chest wound. (5) Over the guidewire 22, dilate (at about 6-8 French) the tract and venotomy, using this step to measure the length of the catheter for insertion. (6) Dilate the subcutaneous tissues using additional short dilators (length approximately 4 cm, diameters up to 30-40 French), creating a pocket for the port segment that may be slightly smaller than the port itself. (7) Advance the separate catheter of the standard portacath system over the guidewire 22 into position, then remove the guidewire 22. Attach the hub/port, proximal subcutaneous hub 15, to the catheter. Advance the mated port and catheter until the port is in the subcutaneous tissues and the catheter further within the central veins. (8) Access the port with a Huber needle and flush the port. (9) Close the cranial incision, which may be accomplished with 1 or 2 stitches, a Steri-strip, Dermabond, or some combination. (10) Close the new chest incision, which may be accomplished with one subcutaneous buried resorbable suture, a Steri-Strip, Dermabond, or some combination. The old chest wound is allowed to heal by secondary intention.

With respect to the shape of the hub/port, proximal subcutaneous hub 15, used in any embodiment, as previously noted, the shape may not be a cylinder, but the use of dilators to create a pocket would still be possible. Standard dilators with a circular cross section could be used to create a pocket for a proximal subcutaneous hub 15 or separate port that is not cylindrical. In addition, dilators themselves could have a non-circular cross section, ovoid, trapezoidal, or other shape, in order to create a pocket for a proximal subcutaneous hub 15 or port that is not cylindrical.

There is added benefit when the implanted catheter device 10 not only preserves access but also can be used for infusions and medication administration. This is because venous access for dialysis patients is broadly problematic: these patients P have comorbidities that often require venous access for medications, but peripheral access is typically difficult and may also be injurious to peripheral veins. In turn, injury to peripheral veins further limits access options for arm fistulas and grafts.

The implanted catheter device 10 of the invention could be useful to maintain a pathway as a place keeper even if there were no straightforward mechanism to insert a new HD catheter C from the implanted catheter device 10 of the invention. It would be possible to perform a cut-down along any portion of the implanted catheter device 10, to free the catheter at any point, and to advance a guidewire 22 through that segment to the venous system, such as the superior vena cava/right atrial junction. While this process would be more laborious and time-consuming, the catheter device 10 would still have achieved a primary mission of maintaining a path from the subcutaneous tissues to venous system, such as the superior vena cava or right atrium.

It should be recognized that some modifications on each element of the invention could be made without circumventing the invention system. The core elements of the system are (1) the method of alternating between a large, internal/external HD catheter C and a smaller fully internal place keeper device, such as the catheter device 10, and (2) designing the catheter device 10 to be placed easily, in most embodiments over a guidewire 22, and feature a relatively small intravenous segment of the distal portion 11 that would be less likely than an HD catheter C to cause any complications, such as thrombosis and hyperplasia, caused by a catheter C. There are various ways to design the detachable pusher device 60, the retention mechanism, the methods of converting the implanted catheter device 10 to a catheter C, vice versa, converting to an infusion device, and so on.

The method of the invention is to alternate between an internal/external catheter C, such as an HD catheter, and a fully internal catheter device 10 of the invention. This is a novel practice that is not a part of current patient P care. For perspective, in current practice, it is not at all unusual for an internal/external hemodialysis catheter C to be exchanged over a guidewire 22 for a new internal/external catheter C. However, it is rare for an internal/external catheter C to be directly exchanged for a fully internal device. And unknown to date, for an internal/external catheter C to be directly exchanged for a fully internal catheter device 10, whereby it acts to be a placekeeper device. It is also rare for a fully internal catheter, such as a portacath, to be exchanged for an internal/external catheter C. Conversely, the method of the invention is, by design, to repeatedly alternate exchanges of an internal/external catheter C with fully internal catheter device 10 of the invention.

The placekeeper catheter device 10 would be of clear benefit to a patient P who is running out of access options, but it should also be useful earlier in a lifetime of dialysis. For example, if the catheter device 10 were used after an initial access via a right jugular vein, then a subsequent availability of the right jugular vein would be ensured, which is not the case with current practices. The ability to re-use the same, most favorable access repeatedly should decrease the use of catheters C in less favorable locations in the patient P. Further, prolonging the availability of each access site in the patient P would almost certainly increase the lifetime options for access, and make it unlikely that a patient would reach a point at which access for HD would no longer be possible.

Another beneficial use of the catheter device 10 would occur if there is a pacemaker in place. A pre-existing pacemaker limits access options for dialysis patients, since the wires are associated with a high risk of intimal hyperplasia and vein occlusion. In that setting, a surgeon will generally place a graft or fistula on the side opposite the pacemaker. Catheter C placement options are therefore limited, and the preservation of access becomes more important.

Another potential benefit of the catheter device 10 would be in the setting of placement of a hemodialysis reliable outflow (HeRO) graft access system. These devices are intended to provide graft access in a patient who has diseased central veins, with a catheter segment that crosses the central veins to provide venous return to the SVC or RA. However, in order to place a HeRO graft, the operator must first establish a pathway across the central veins. Therefore, if there is severe disease or an occlusion, the catheter device 10 of the invention could be used to provide a pathway for the placement of a HeRO device. Conversely, if the HeRO is eventually abandoned, the catheter device 10 of the invention could be exchanged back in to maintain central venous access for future needs.

Another benefit of the catheter device 10 is safety. Whenever a new catheter C is placed, the portion of the procedure associated with the highest risk is during needle cannulation of a vein and subsequent passage of a guidewire 22 toward the SVC. While unusual, case reports describe inadvertent passage of a guidewire 22 and catheter C into the mediastinum, pericardium and aorta, with catastrophic results. Conversely, once a safe vein pathway is established, use of the catheter device 10 of the invention would avoid these steps in catheter C placement, so the risk of significant complication would be reduced.

The implanted catheter device 10 functions as a placekeeper to be exchanged for other catheters C. However, as described above, an additional embodiment of the implanted catheter device 10 could itself function to provide venous access while implanted. There are two (2) mechanisms whereby this could occur, either via an embodiment FIG. 7, wherein (1) the proximal subcutaneous hub 15 can be accessed percutaneously after placement, or (2) via conversion of fully internal catheter device 10 of the invention for and internal/external catheter C for infusions.

With respect to conversion of the catheter device 10 into an internal/external catheter C device, this could be accomplished via the same mechanism proposed to perform exchange of the catheter device 10 of the invention for a hemodialysis catheter C. The detachable pusher device 60 described above as a part of a catheter exchange could be attached to the catheter device 10 using a small incision I and blunt dissection. After attachment, the assembled implantable catheter system, having the detachable pusher device 60 proximal back end would be external and available for attachment, such as to the screw configuration for attachment 25*a*, to an intravenous line or for direct syringe injection.

While the catheter device 10 of the invention has been depicted as placed at the time of a hemodialysis catheter C removal, it would also be straightforward to place the catheter device 10 de novo, meaning an implanted pre-existing catheter C is not priorly present before implantation of the catheter device 10, wherein the step of removing the implanted pre-existing catheter Cis absent and inserting the guidewire 22 creates its own de-novo tract to the venous system. While this is less likely in practice, there could be circumstances in which the practitioner needs to establish access for future use at a time other than a catheter C removal.

A method example is provided as a guide and is non-limiting, wherein a method of maintaining a venous access pathway, wherein a pre-existing catheter C is exchanged for a catheter device 10, the method comprising:

1. providing a catheter device 10 comprising:
   a. a proximal subcutaneous hub 15, a distal portion 11 and a lumen 12, wherein:
      i. an outer-diameter of the proximal subcutaneous hub 15 is larger than an outer-diameter of the distal portion 11;
      ii. the proximal subcutaneous hub 15 comprising a retention system;

iii. the lumen 12 extending from an opening of the lumen at the proximal terminus 12*b* of the proximal subcutaneous hub 15 to an opening of a lumen at the distal terminus 12*a* of the distal portion 11 and comprises an inner diameter and a valve 17;

2. further providing a detachable pusher device 60;
3. further providing a guidewire 22;
4. assembling an implantable catheter system by attaching the detachable pusher device 60 to the catheter device 10;
5. inserting a guidewire 22 through a lumen of the pre-existing catheter C into the venous pathway;
6. removing the pre-existing catheter C over the guidewire 22;
7. inserting a peel-away sheath 30 over the guidewire 22;
8. inserting the assembled implantable catheter system over the guidewire 22 via the peel-away sheath 30 into the venous pathway;
9. removing the peel-away sheath 30;
10. deploying the retention system (optional);
11. removing the guidewire 22 from the implantable catheter system;
12. flushing the catheter device 10 by engaging the proximal back end of the detachable pusher device 60, i.e., attach a syringe;
13. disassembling and removing the detachable pusher device 60 from the catheter device 10;
14. packing the wound with iodophor gauze (optional);
15. closing the wound or incision, e.g., by permitting the chest wound to close over time by secondary intention, suturing, butterflying, stapling, etc.

A method example is provided as a guide and is non-limiting, wherein the catheter device 10 is exchanged for a new hemodialysis catheter C, comprising the following steps:

1. Providing a patient P having an implanted catheter device 10;
2. Performing a first incision Ia of the skin at the proximal subcutaneous hub 15;
3. Freeing the retention system, such as the retention cuff 13, using blunt dissection;
4. Performing a second incision Ib just below the proximal subcutaneous hub 15;
5. Delivering a detachable pusher device 60 from the second incision Ib to the first incision Ia,
6. Mating the detachable pusher device 60 to the catheter device 10 to make the assembled implantable catheter system;
7. Advancing a guidewire 22 via the lumen 12 of the implantable catheter system from the back end of the detachable pusher device 60 through the catheter device 10 into the venous system;
8. Removing the implantable catheter system over the guidewire 22;
9. Dilating the vacated subcutaneous tract and intravenous pathway traced by the guidewire 22 using dilators, angioplasty, or a combination thereof;
10. Inserting a peel-away sheath 30 over the guidewire 22;
11. Inserting the new HD catheter C via the peel-away sheath 30 over the guidewire 22 into the venous system;
12. Removing the peel-away sheath 30;
13. Closing incisions Ia and Ib.

A method example is provided as a guide and is non-limiting, wherein an implanted catheter device 10 is converted into an infusion catheter and reverting said infusion catheter to a implanted catheter device 10, the method comprising:

1. providing a patient having a implanted catheter device 10 comprising a proximal subcutaneous hub 15 configured for attachment at its proximal terminus, a retention system, a distal portion 11 and a lumen 12;
2. providing a detachable pusher device 60 configured for attachment to the configured proximal terminus of the proximal subcutaneous hub 15 of the catheter device 10;
3. converting a implanted catheter device 10 into an infusion catheter, comprising:
   a. performing a first incision Ia of the skin at the proximal subcutaneous hub 15 of the implantable catheter device 10;
   b. freeing the retention system, e.g., using blunt dissection;
   c. performing a second incision Ib just below the proximal subcutaneous hub 15;
   d. delivering the detachable pusher device 60 from the second incision Ib to the first incision Ia;
   e. attaching the detachable pusher device 60 to the proximal subcutaneous hub 15 of the implantable catheter device 10 to make the mated catheter system;
4. using the infusing catheter by attaching a reservoir to the back end of the detachable pusher device 60, e.g., attaching a syringe, a catheter, etc.
5. reverting an infusion catheter to a implanted catheter device 10, comprising:
   a. detaching the detachable pusher device 60 from the proximal subcutaneous hub 15;
   b. closing any incisions.

A method example is provided as a guide and is non-limiting, wherein a method of converting a catheter device 10 into an intravenous access device, the method comprising:

1. providing a catheter device 10 comprising a proximal subcutaneous hub 15, a distal portion 11, and a lumen 12, further comprising:
   a. a luminal chamber 50 in the proximal subcutaneous hub 15, wherein the luminal chamber 12*c* is continuous with the lumen 12 of the catheter device 10 and comprises an access region 52 to the luminal chamber 12*c* in the proximal subcutaneous hub 15 and a wall thickness of the access region 51, and wall thickness of the proximal subcutaneous hub with the luminal chamber 51*a;*
   b. the access region 52 is surrounded by a radiopaque annular ring 55;
   c. the access region 52 comprising a drum 54;
   d. the radiopaque annular ring 55 is in an asymmetrical association in respects to the location of a radiopaque marker 13 (optional);
   e. the wall thickness of the proximal subcutaneous hub with the luminal chamber 51*a* is thicker than the wall thickness of the access region 51 (optional);
      i, wherein the wall thickness of the proximal subcutaneous hub with the luminal chamber 51*a* is thicker comprising of a material resistant to puncture by a needle;
2. implanting the catheter device 10;
3. locating the access region 52 using the radiopaque annular ring 55 and/or the radiopaque marker 13;
4. accessing the luminal chamber 12*c*.

A method example is provided as a guide and is non-limiting, wherein a method of converting a hemodialysis catheter C into a catheter device 10 into an intravenous access portacath device via a separate tunnel, the method comprising:

(1) After lidocaine infiltration, make a small incision over a cranial segment of the existing catheter, freeing the catheter.

(2) Cut the catheter C, then advance a guidewire through the cranial portion into the central veins. Remove the back end of the existing catheter.

(3) After lidocaine infiltration, make a 1.5 cm incision approximately 4-5 cm below the clavicle, adjacent to but distinct from the exit site of the original catheter.

(4) Tunnel a device from the chest wound to the cranial incision, and then deliver the back end of the guidewire 22 from the venotomy to the new chest wound.

(5) Over the guidewire 22, dilate (at about 6-8 French) the tract and venotomy, using this step to measure the length of the catheter for insertion.

(6) Dilate the subcutaneous tissues using additional short dilators (length approximately 4 cm, diameters up to 30-40 French), creating a pocket for the port segment that is slightly smaller than the port itself.

(7) Advance the portacath of the invention over the guidewire 22 into position, the port in the subcutaneous tissues and the catheter within the central veins.

(8) Remove the guidewire 22 and flush the port via the guidewire portal.

(9) Close the cranial incision, which may be accomplished with 1 or 2 stitches, a Steri-strip, Dermabond, or some combination.

(10) Close the new chest incision, which may be accomplished with one subcutaneous buried resorbable suture, a Steri-Strip, Dermabond, or some combination. The old chest wound is allowed to heal by secondary intention.

A method example is provided as a guide and is non-limiting, wherein a method of placing the catheter device di novo, which includes the di novo placement of the embodiment in which the catheter device functions as a portacath, the method comprising:

(1) After lidocaine infiltration, make a small incision over a vein for access, usually the right internal jugular vein.

(2) Select the vein via the incision using a needle, usually done using ultrasound guidance, and then pass a guidewire 22 through the needle into the central veins.

(3) After lidocaine infiltration, make a 1.5 cm incision approximately 4-5 cm below the clavicle.

(4) Tunnel a device from the chest wound to the venotomy, and then deliver the back end of the guidewire 22 from the venotomy to the chest wound.

(5) Over the guidewire 22, dilate (at about 6-8 French) the tract and venotomy, using this step to measure the length of the catheter for insertion.

(6) Dilate the subcutaneous tissues using additional short dilators (length approximately 4 cm, diameters up to 30-40 French), creating a pocket for the port segment that is slightly smaller than the port itself.

(7) Advance the portacath, catheter device 10. of the invention over the guidewire 22 into position, the port in the subcutaneous tissues and the catheter within the central veins.

(8) Remove the guidewire 22 and flush the port via the guidewire portal.

(9) Close the neck incision, which may be accomplished with 1 or 2 stitches, a Steri-strip, Dermabond, or some combination.

(10) Close the chest incision, which may be accomplished with one subcutaneous buried resorbable suture, a Steri-Strip, Dermabond, or some combination.

A method example is provided as a guide and is non-limiting, wherein a method of converting a hemodialysis catheter C into a non-over-the-wire (standard) portacath using the cylindrical hub with wings port shape, e.g., proximal subcutaneous hub 15 having an access region 52, luminal chamber 12*c*, and wings, the method comprising:

(1) After lidocaine infiltration, make a small incision over a cranial segment of the existing catheter C, freeing the catheter C.

(2) Cut the catheter, then advance a guidewire 22 through the cranial portion into the central veins. Remove the back end of the existing catheter.

(3) After lidocaine infiltration, make about a 1.5 cm incision approximately 4-6 cm below the clavicle, adjacent to but distinct from the exit site of the original catheter C.

(4) Tunnel a grabber device or other mechanism from the chest wound to the cranial incision, and then deliver the back end of the guidewire 22 from the venotomy to the new chest wound.

(5) Over the guidewire 22, dilate (at about 6-8 French) the tract and venotomy, using this step to measure the length of the catheter for insertion.

(6) Dilate the subcutaneous tissues using additional short dilators (length approximately 4 cm, diameters up to 30-40 French), creating a pocket for the port segment that may be slightly smaller than the port itself.

(7) Advance the separate catheter of the standard portacath system over the guidewire 22 into position, then remove the guidewire 22. Attach the hub/port, proximal subcutaneous hub 15, to the catheter. Advance the mated port and catheter until the port is in the subcutaneous tissues and the catheter further within the central veins.

(8) Access the port with a Huber needle and flush the port.

(9) Close the cranial incision, which may be accomplished with 1 or 2 stitches, a Steri-strip, Dermabond, or some combination.

(10) Close the new chest incision, which may be accomplished with one subcutaneous buried resorbable suture, a Steri-Strip, Dermabond, or some combination. The old chest wound is allowed to heal by secondary intention.

A method example is provided as a guide and is non-limiting, wherein a method of a de novo placement of a non-over-the-wire (standard) portacath using the cylindrical hub with wings port shape, e.g., proximal subcutaneous hub 15 having an access region 52, luminal chamber 12*c*, and wings, the method comprising:

(1) After lidocaine infiltration, make a small incision over a vein for access, usually the right internal jugular vein.

(2) Select the vein via the incision using a needle, usually done using ultrasound guidance, and then pass a guidewire 22 through the needle into the central veins.

(3) After lidocaine infiltration, make about a 1.5 cm incision approximately 4-6 cm below the clavicle, adjacent to but distinct from the exit site of the original catheter C.

(4) Tunnel a grabber device or other mechanism from the chest wound to the cranial incision, and then deliver the back end of the guidewire 22 from the venotomy to the new chest wound.

(5) Over the guidewire 22, dilate (at about 6-8 French) the tract and venotomy, using this step to measure the length of the catheter for insertion.

(6) Dilate the subcutaneous tissues using additional short dilators (length approximately 4 cm, diameters up to 30-40 French), creating a pocket for the port segment that may be slightly smaller than the port itself.

(7) Advance the separate catheter of the standard porta-cath system over the guidewire 22 into position, then remove the guidewire 22. Attach the hub/port, proximal subcutaneous hub 15, to the catheter. Advance the mated port and catheter until the port is in the subcutaneous tissues and the catheter further within the central veins.

(8) Access the port with a Huber needle and flush the port.

(9) Close the cranial incision, which may be accomplished with 1 or 2 stitches, a Steri-strip, Dermabond, or some combination.

(10) Close the new chest incision, which may be accomplished with one subcutaneous buried resorbable suture, a Steri-Strip, Dermabond, or some combination. The old chest wound is allowed to heal by secondary intention.

What is claimed is:

1. A method of maintaining a venous access pathway in a patient, wherein an implanted pre-existing catheter is present in the patient and enters the patient through an incision, the method comprising:

providing a catheter device comprising:

a proximal subcutaneous hub portion, a distal portion, and a lumen, wherein:

an outer-diameter of the proximal subcutaneous hub is larger than an outer-diameter of the distal portion, wherein there is a step down or a taper between the outer-diameter of the proximal subcutaneous hub and the outer-diameter of the distal portion;

the proximal subcutaneous hub comprising a retention system;

the lumen extends from an opening of the proximal subcutaneous hub to an opening of the distal portion and comprises an inner diameter and a mechanism to prevent flow of fluid through the lumen;

wherein the catheter device is fully implantable;

inserting a guidewire through the implanted pre-existing catheter reaching into the venous system;

exchanging the implanted pre-existing catheter comprising:

removing the implanted pre-existing catheter over the guidewire and implanting the catheter device, wherein the implantation of the catheter device further comprises assembling an implantable catheter system by attaching a detachable pusher device to the proximal subcutaneous hub of the catheter device, wherein the detachable pusher device and the catheter device are configured to be attached to each other;

wherein the detachable pusher device has a lumen from its proximal to its distal end and the detachable pusher device is configured to align the lumen of the detachable pusher device with the lumen of the catheter device when the detachable pusher device is attached to the proximal subcutaneous hub of the catheter device; and wherein the implantation of the catheter device further includes advancing the assembled catheter and pusher device centrally, so that the catheter is fully internal in the patient after the pusher device has been disconnected and removed.

2. The method of maintaining a venous access pathway of claim 1, further comprises inserting the assembled implantable catheter system over the guidewire until the distal portion enters the venous system.

3. The method of maintaining a venous access pathway of claim 2, further comprises inserting a peel-away sheath over the guidewire and inserting the assembled implantable catheter system over the guidewire using the peel-away sheath and removing the peel-away sheath.

4. The method of maintaining a venous access pathway of claim 2, further comprises deploying the retention system.

5. The method of maintaining a venous access pathway of claim 2, further comprises removing the guidewire and optionally flushing the assembled implantable catheter system by engaging the proximal back end of the detachable pusher device.

6. The method of maintaining a venous access pathway of claim 5, further comprises disassembling the implantable catheter system and removing the detachable pusher device from the catheter device.

7. The method of maintaining a venous access pathway of claim 6, further comprises adding antimicrobial material and packing the wound.

8. The method of maintaining a venous access pathway of claim 2, wherein the pusher device is promptly removed at the time of insertion of the catheter device.

9. The method of maintaining a venous access pathway of claim 2, wherein the detachable pusher device remains mated with the catheter device for some period of time after catheter insertion, and then it is subsequently disassembled and removed during a separate session.

10. The method of maintaining a venous access pathway of claim 1, wherein the method further comprises infusing fluid using the implanted catheter system.

11. The method of maintaining a venous access pathway of claim 1, wherein a portion or portions of the proximal subcutaneous hub may be flattened.

12. The method of maintaining a venous access pathway of claim 1, wherein the proximal subcutaneous hub has a cross-section and wherein the cross-section is circular, oval, square, rhomboid, triangular, or tear drop.

13. The method of maintaining a venous access pathway of claim 1, wherein the proximal subcutaneous hub comprises flat wings extending from the front (distal) or back (proximal) of the proximal subcutaneous hub.

14. The method of maintaining a venous access pathway of claim 1, wherein the mechanism to prevent flow of fluid through the lumen comprises a valve.

15. The method of maintaining a venous access pathway of claim 1, wherein the mechanism to prevent flow of fluid through the lumen is configured with a screw.

16. The method of maintaining a venous access pathway of claim 1, wherein the distal portion is coated with a coating to prevent it from becoming stuck in the venous access pathway.

17. The method of maintaining a venous access pathway of claim 1, wherein the catheter device is coated with a coating to prevent infection.

18. The method of maintaining a venous access pathway of claim 1, wherein the outer-diameter of the distal portion is chosen from the group consisting of 2.5 French, 3 French, about 4 French, about 5 French, about 7 French, and about 8 French.

19. The method of maintaining a venous access pathway of claim 1, wherein the configuration for the attachment of the detachable pusher device and the catheter device comprises a screw configuration or luer lock.

20. The method of maintaining a venous access pathway of claim 4, wherein the detachable pusher device is configured to actuate deployment of the retention system from a constrained configuration to an expanded configuration after placement of the catheter device in a subcutaneous tract.

21. The method of maintaining a venous access pathway of claim 1, wherein insertion of the assembled implantable catheter system over the guidewire comprises advancing the catheter device through an existing skin incision and an existing subcutaneous tract previously occupied by the implanted pre-existing catheter without creating a separate new incision for the catheter device.

22. The method of maintaining a venous access pathway of claim 1, wherein the outer diameter of the proximal subcutaneous hub is in the range between 14 French to 17 French.

23. The method of maintaining a venous access pathway of claim 1, wherein the outer diameter of the proximal subcutaneous hub is up to 20 French.

24. The method of claim 1, comprising further advancing the catheter device over the guidewire through the incision and through an existing subcutaneous tract previously occupied by the pre-existing catheter, without creating a separate new incision for the catheter device.

25. The method of claim 24, wherein advancing the catheter device over the guidewire comprises creating a separate incision spaced from the prior skin incision associated with the pre-existing catheter device, forming a separate tunnel from the separate incision to the venous pathway, and routing a proximal portion of the guidewire through subcutaneous tissue to exit at the separate incision while a distal portion of the guidewire remains within the venous pathway, and advancing the catheter device over the guidewire through the separate tunnel into the venous pathway.

26. The method of claim 1, wherein the proximal subcutaneous hub comprises a retention system configured to resist movement of the hub relative to a subcutaneous tract, wherein the retention system comprises at least one of:

(a) a self-expanding flanges movable from a constrained configuration during insertion to an unconstrained configuration after implantation;

(b) an expandable retention element configured to be expanded after positioning; or (c) the proximal subcutaneous hub having a maximum outer diameter of about 20 to 70 French that contributes towards anchoring the catheter device.

27. The method of maintaining a venous access pathway of claim 1, wherein the outer diameter of the proximal subcutaneous hub is in the range between about 10 mm and about 14 mm.

28. The method of maintaining a venous access pathway of claim 1, wherein a guidewire is re-routed to a new, separate skin incision and separate subcutaneous tunnel, followed by insertion of the assembled implantable catheter system over the re-routed guidewire.

29. The method of maintaining a venous access pathway of claim 1, wherein the proximal subcutaneous hub comprises two flat wings extending from the back (proximal) of the proximal subcutaneous hub and wherein the wings are configured to have a rocket fin-like shape.

30. The method of maintaining a venous access pathway of claim 29, wherein the flat wings are expanding wings.

* * * * *